US012562245B2

(12) United States Patent
Sukhtipyaroge

(10) Patent No.: US 12,562,245 B2
(45) Date of Patent: Feb. 24, 2026

(54) ARTIFICIAL INTELLIGENCE-BASED MEDICAL CODING AND DIAGNOSIS

(71) Applicant: MatrixCare, Inc., Bloomington, MN (US)

(72) Inventor: Nate Sukhtipyaroge, Bloomington, MN (US)

(73) Assignee: MatrixCare, Inc., Bloomington, MN (US)

( * ) Notice: Subject to any disclaimer, the term of this patent is extended or adjusted under 35 U.S.C. 154(b) by 429 days.

(21) Appl. No.: 17/566,503

(22) Filed: Dec. 30, 2021

(65) Prior Publication Data

US 2023/0215523 A1     Jul. 6, 2023

(51) Int. Cl.
*G16H 10/60*          (2018.01)
*G16H 50/20*          (2018.01)
(52) U.S. Cl.
CPC ............. *G16H 10/60* (2018.01); *G16H 50/20* (2018.01)
(58) Field of Classification Search
None
See application file for complete search history.

(56) References Cited

U.S. PATENT DOCUMENTS

| | | | |
|---|---|---|---|
| 11,875,883 B1* | 1/2024 | Perez | G16H 50/20 |
| 2016/0239617 A1* | 8/2016 | Farooq | G16H 10/60 |
| 2018/0247024 A1* | 8/2018 | Divine | G16H 40/20 |
| 2019/0130073 A1* | 5/2019 | Sun | G16H 10/60 |
| 2021/0027889 A1* | 1/2021 | Neil | G16H 10/60 |
| 2022/0059224 A1* | 2/2022 | Tulley | G10L 15/26 |

OTHER PUBLICATIONS

Fages, Stages of a Human-in-the-Loop Machine Learning Application, May 26, 2020, https://thenewstack.io/stages-of-a-human-in-the-loop-machine-learning-application/ (Year: 2020).*
IBM, Mainframe Concepts, 2006, z/OSBasicSkills InformationCenter, p. 10 (Year: 2006).*

* cited by examiner

*Primary Examiner* — Devin C Hein
(74) *Attorney, Agent, or Firm* — Patterson + Sheridan, LLP

(57)          ABSTRACT
Techniques for improved machine learning are provided. Patient data for a patient is received, the patient data relating to an action performed by a caregiver. A medical code is generated for the action by processing the patient data using a machine learning model, and the action is associated with the medical code. An event record, including the medical code, is generated for the patient.

24 Claims, 15 Drawing Sheets

Generate a predicted code using a model — 905

Compute a loss between predicted code and actual code — 910

Refine model parameter(s) based on loss — 915

1100

1300

Receive patient data for a patient, the patient data relating to an action performed by a caregiver          1305

Generate a medical code for the action by processing the patient data using a machine learning model          1310

Associate the action with the medical code          1315

Generate an event record, including the medical code, for the patient          1320

1400

Receive patient data for a first patient, the patient data corresponding to an action performed by a caregiver — 1405

Identify a medical code entered by a caregiver in association with the action — 1410

Label the patient data based on the medical code — 1415

Train a machine learning model, based on the labeled patient data, to generate medical codes — 1420

ARTIFICIAL INTELLIGENCE-BASED MEDICAL CODING AND DIAGNOSIS

INTRODUCTION

Embodiments of the present disclosure relate to machine learning and artificial intelligence. More specifically, embodiments of the present disclosure relate to using artificial intelligence to perform medical coding and diagnosis.

In a wide variety of medical settings, users (e.g., caregivers, nurses, doctors, and the like) are often expected to record or otherwise preserve indications of their interactions with patients, including the actions the caregiver takes, diagnoses made, and the like. This data can generally be used to preserve a concrete record of the patient's status, the tasks performed, when they were performed, who performed them, and the like. Additionally, in some settings, the user must further record or indicate predefined classifications, categories, or codes for the action(s) performed, the diagnosis of the patient, the state of the patient, and the like. However, given the large number of tasks performed by each user, as well as the vast number of alternative classifications and categories, it is generally difficult or impossible to record all such tasks and codes immediately after performing them.

As a result, significant inaccuracies and missed items are present in the conventional records (e.g., due to forgotten or misremembered tasks, mislabeled tasks, and the like). Inaccuracies in these records can have a wide variety of long-reaching impacts.

Improved systems and techniques to automatically classify and code such tasks are needed.

SUMMARY

According to one embodiment presented in this disclosure, a method of using machine learning to perform medical coding. The method comprises: receiving patient data for a patient, the patient data relating to an action performed by a caregiver; generating a medical code for the action by processing the patient data using a machine learning model; associating the action with the medical code; and generating an event record, including the medical code, for the patient.

According to one embodiment presented in this disclosure, a method of training machine learning models is provided. The method comprises: receiving patient data for a first patient, the patient data corresponding to an action performed by a caregiver; identifying a medical code entered by a caregiver in association with the action; labeling the patient data based on the medical code; and training a machine learning model, based on the labeled patient data, to generate medical codes.

The following description and the related drawings set forth in detail certain illustrative features of one or more embodiments.

DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
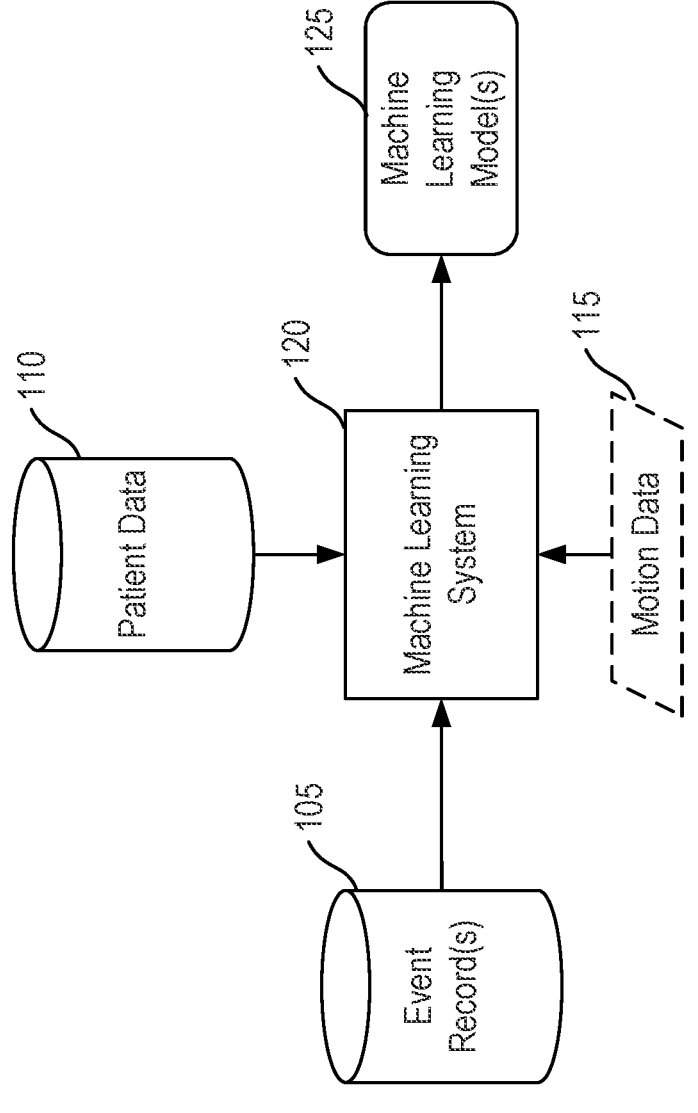
FIG. 1 depicts an example environment for training machine learning models to evaluate patient data and generate medical codes.

Aspects of the present disclosure provide apparatuses, methods, processing systems, and computer-readable mediums for improved machine learning models for performing medical coding and diagnostics.

Accurate coding is a tremendously impactful problem in a wide variety of medical settings. As used herein, coding refers to the process of assigning defined codes, classifications, categories, or other labels to various patient data (e.g., to actions performed, to indicate what a healthcare visit was for and what was done, to indicate diagnosis, and the like). In some embodiments, coding refers to selecting one or more codes from a defined set of medical codes, such as from one or more versions of the International Statistical Classification of Diseases and Related Health Problems (ICD) code (e.g., ICD-10, ICD-11, ICD-10-CM, and the like).

For example, using ICD-10-CM, a healthcare professional may treat a patient after a head injury, and code the visit or action as S06.0XA, which indicates "concussion with loss of consciousness of 30 minutes or less, initial encounter." In embodiments, there may be a vast number of such codes (e.g., well into the tens of thousands), each with varying levels of specificity. Additionally, many codes are quite similar, and it can be difficult or impossible for the user to accurately and efficiently identify which code(s) apply to a given situation.

In embodiments, accurate coding can be highly important for a variety of reasons, including to ensure that healthcare providers have a full and accurate picture of the patient's state. Additionally, in some cases, medical billing requires use of these codes. For example, to file an insurance claim or for payment from systems such as Medicaid, the user must generally include the relevant code(s) to ensure payment. Not only can inaccurate coding result in denied payment, but in some cases, the specificity of the code can impact the payment amount, if any. For example, some payers require specific and granular coding to ensure payment, and either refuse payment or offer reduced reimbursement for more high-level codes, even if the higher-level codes are accurate.

In some embodiments of the present disclosure, machine learning models are trained and used to generate accurate coding for patient data. For example, based on data such as the patient's lab results, radiology results, written assessments or notes from the healthcare provider, and the like, the system can use machine learning to automatically identify and apply relevant medical code(s) (e.g., from ICD-10, ICD-10-CM, and/or ICD-11), enabling automated generation of accurate and complete event records indicating the status of the patient and the actions or tasks performed.

In embodiments, the system is thereby able to reduce wasted effort (e.g., allowing the healthcare provider to continue to other tasks), improve coding accuracy, and improve any further analysis or evaluation that is performed based (at least in part) on the codes. For example, downstream systems may use the codes to quickly identify relevant patients or information for specific disorders, such as to facilitate clinical studies, to train other machine learning models, and the like.

In some embodiments, the system is further able to use the generated codes to assist in diagnosing and/or treating patients. In at least one embodiment, the system can determine whether the medical issue(s) associated with any generated code are already indicated in the patient's data. If not, the system may diagnose (or suggest diagnosis) of the issue, select and facilitate treatments, and the like. For example, based on various patient data, the system may automatically assign a code such as A77.0, "spotted fever due to *Rickettsia rickettsii*." If the system then determines that the patient has not already been formally diagnosed with this tick-borne illness, the system may proceed to diagnose the patient, suggest the diagnosis to the healthcare provider, select one or more treatments, and the like.

Example Environment for Training Machine Learning Models to Evaluate Patient Data and Generate Medical Codes FIG. 1 depicts an example environment 100 for training machine learning models to evaluate patient data and generate medical codes.

In the illustrated environment 100, a set of event records 105 and patient data 110 are provided to a machine learning system 120. The machine learning system 120 may generally correspond to one or more physical devices or components, one or more software components, or a combination of hardware and software. In some embodiments, the machine learning system 120 executes in a cloud-based deployment.

The event records 105 generally correspond to specific times when a healthcare provider performed some action or intervention for a patient, such as during a healthcare visit. For example, a first event record may correspond to a patient attending a doctor's appointment for a check-up, for preventative care (e.g., vaccination), to address a medical concern or issue (e.g., persistent headaches), and the like.

Similarly, a given event record may correspond to a healthcare provider (e.g., a nurse or caregiver) performing some action to assist, treat, or aid the user, such as a nurse examining and treating a wound of a resident in a long-term residential care facility (e.g., a nursing home). In some embodiments, each event record 105 can include some contextual information for the event, such as the identity of the patient and/or healthcare provider, the reason for the visit, any diagnoses that were determined, action(s) taken, medication(s) prescribed, and the like.

In some embodiments, the event records 105 can also include one or more medical codes (e.g., selected or designated by the healthcare provider). For example, based on the context of the visit or event, the user may select one or more appropriate codes to specifically indicate the patient's state (e.g., the issue, disorder, or concern), the action(s) that were performed (e.g., monitoring, treating, cleaning, stitching a wound, etc.), and the like. As discussed above, these codes may include ICD codes, such as S01.01XA from ICD-10-CM, which indicates "laceration without foreign body of scalp, initial encounter." As discussed above, these defined codes can be useful or required for a variety of uses, such as for medical billing, to identify and sort relevant records in a computationally efficient and quick manner, and the like.

In the illustrated example, the machine learning system 120 also receives a set of patient data 110. Generally, the patient data 110 can include broader information about one or more patients. For example, while the event records 105 may indicate the specific context of a specific visit (e.g., the lab results determined in association with that visit), the patient data 110 may more generally indicate other relevant patient data, such as their biographical information (e.g., age, gender, height, weight, and the like), previous diagnoses, previous and/or current medications, and the like.

Although depicted as discrete records for conceptual clarity, in some embodiments, the patient data 110 and event records 105 may in fact be stored in the same repository. For example, the patient data 110 for a given patient may be represented at least in part as a set or sequence of event records 105 for the patient, showing the patient's health over time.

As illustrated, the machine learning system 120 may optionally receive motion data 115 as well. The motion data 115 may generally be collected via one or more motion sensors configured to record motion data from one or more users (e.g., healthcare providers). For example, the motion sensors may be accelerometers included in wearable devices, such as wrist-wearable devices (e.g., smart watches). In an embodiment, the motion sensors are generally configured to capture motion data of the user's arms, hands, and/or fingers. In embodiments, there may be any number of motion sensors used by each user. For example, the system may use two motion sensors per user (e.g., one on each wrist), and there may be any number of users that are used to generate training data.

In the illustrated example, the motion data 115 may generally be indicative of the orientation of one or more parts (e.g., the hands or arms) of a user at various points in time, movement of these parts (which may include the direction of movement and/or the acceleration or speed of the movement), and the like. In one embodiment, the motion data can be evaluated using one or more trained machine learning models to identify the particular action(s) being performed by the user, which may enable more accurate coding. For example, the motion data 115 may be parsed to determine or infer that the user was using an otoscope (e.g., to examine the patient's ear). As discussed in more detail below, this motion or action can therefore be useful in identifying the appropriate code (e.g., H92.02, indicating "otalgia, left ear").

As illustrated, the motion data 115 is included in dashed lines to indicate it as an optional input. That is, in some embodiments, the machine learning system 120 may receive and classify the motion data 115 to determine the action(s) being performed, which can then serve as input to the trained models. In other embodiments, the machine learning system 120 may identify these actions as specified by the user (e.g., specified in the event records 105).

In embodiments, the machine learning system 120 can generally train one or more machine learning models 125 to analyze the event records 105, patient data 110, and/or motion data 115, and/or use trained machine learning models 125 to evaluate this data (as discussed in more detail below with reference to FIG. 5).

In the illustrated embodiment, the machine learning system 120 can use the event records 105 to automatically label some or all of the patient data 110 and/or motion data 115. For example, when the machine learning system 120 receives an event record 105, the machine learning system 120 may determine the medical code(s) indicated in the record. The machine learning system 120 can then use these code(s) as the label or target output for the machine learning models 125. The corresponding input may include other information from the event records 105 (e.g., current vital signs of the patient), motion data 115 (e.g., indicating actions the user performed), patient data 110 (e.g., indicating medications the patient is on), and the like. In this way, the machine learning models 125 can be iteratively trained to generate accurate medical codes based on a variety of input data.

In one embodiment, to train the models, the machine learning system 120 can collect event records 105, patient data 110, and/or motion data 115 over time from any number of users and patients. For example, each user in a facility (e.g., a long term care unit or hospital) can have an associated set of one or more motion sensors providing motion data 115, and event records 105 and patient data 110 from these facilities can be collected as well. In this way, the machine learning system 120 can train the models using a potentially tremendous amount of data, enabling far more accurate classifications.

Generally, as discussed in more detail below, training the machine learning models 125 includes providing some set of input data (e.g., event records 105, patient data 110, and/or motion data 115), such as relevant data for a caregiving interaction with a patient, to generate some predicted output (e.g., a predicted medical code that applies to the caregiving interaction). At early stages of training, this output may be relatively random or unreliable (e.g., due to the random weights and/or biases used to initiate the model). The predicted code (or probability scores of each alternative code) can then be compared against the known ground-truth label of the data (e.g., the actual medical code selected by the user, such as indicated in the event record 105) to generate a loss, and the loss can be used to refine the model (e.g., using back propagation in the case of a neural network).

Generally, this refinement process may be performed individually for each event record or code (e.g., using stochastic gradient descent) or in batches (e.g., using batch gradient descent). Further, in embodiments, the machine learning system 120 can train the machine learning models 125 to operate on various input data depending on the particular implementation. For example, some model(s) may be trained to evaluate only data from the corresponding event record 105 (e.g., only the data that was immediately-relevant to the code), while others may be trained to further evaluate the patient's overall status (indicated in the patient data 110).

In embodiments, once the model(s) are trained, the machine learning system 120 can deploy them for use in real-time. In one embodiment, as discussed above, the models may be trained on one or more systems and deployed to one or more other systems. In other embodiments, the machine learning system 120 can both train the models and use them for inferencing.

Figure 2:
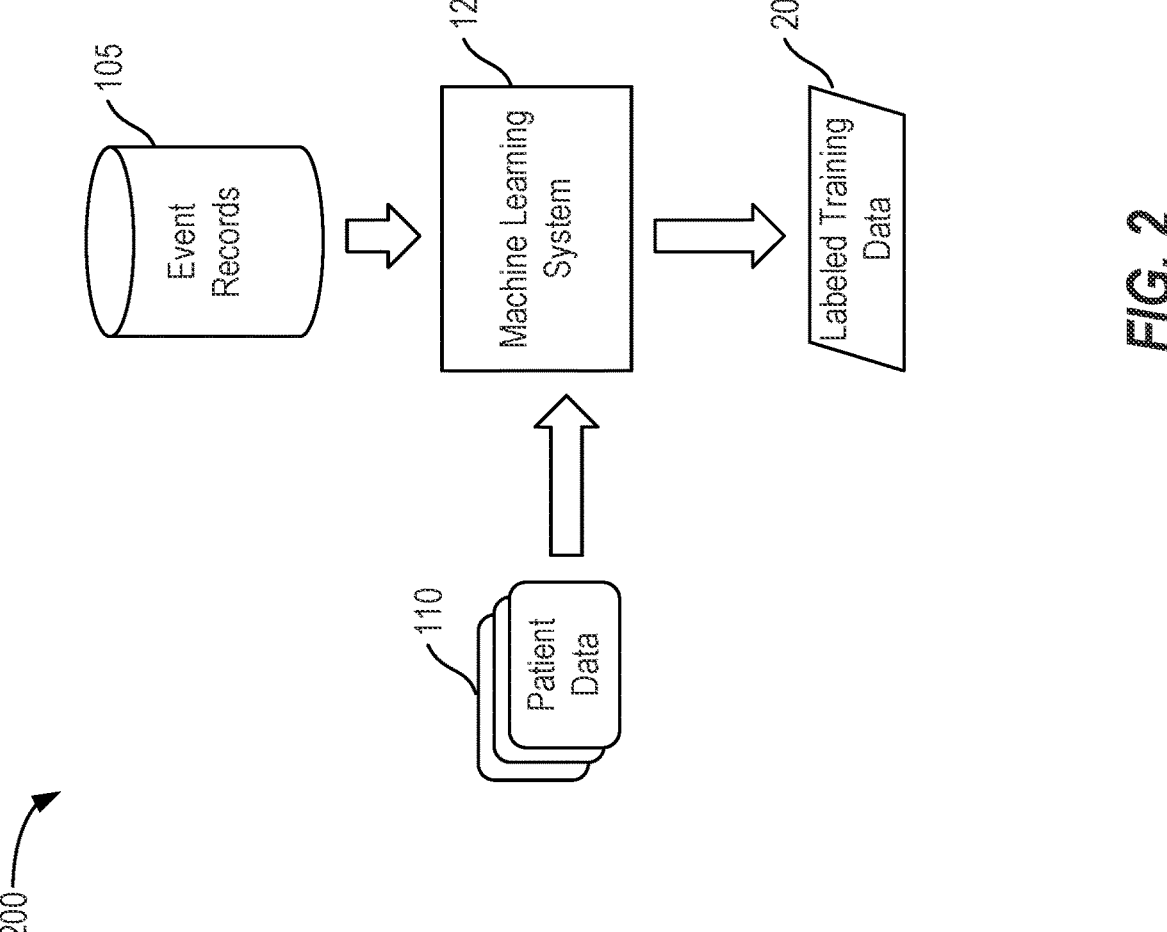
FIG. 2 depicts an example environment for generating labeled data to train machine learning models to perform coding.

Example Environment for Generating Labeled Data to Train Machine Learning Models to Perform Coding FIG. 2 depicts an example environment 200 for generating labeled data to train machine learning models to perform coding.

In the illustrated workflow 200, the machine learning system 120 receives discrete records of patient data 110 and event records 105, and generates labeled training data 205. In an embodiment, as discussed above, the labeled training data 205 may generally correspond to some set of patient data 110 and/or event records 105, associated with a corresponding label indicating the proper medical code for the data.

In some embodiments, the machine learning system 120 may parse the event records 105 to identify action(s) that were performed, interactions with caregivers, and the like. For each such interaction, the machine learning system 120 can identify the code(s) that were assigned to that interaction. Additionally, in some embodiments, the machine learning system 120 can identify or retrieve corresponding patient data from the same patient indicated by the event record 105.

Though not included in the illustrated example, in some embodiments, the machine learning system 120 may also receive motion data for inclusion in the labeled training data 205. In one embodiment, the machine learning system 120 (or another system) can evaluate the motion data (e.g., using trained machine learning model(s)) to identify the action(s) being performed by the user, and include this action in the labeled training data 205. In still another embodiment, the machine learning system 120 (or another system) may classify the motion data based on the action, and add the action to the event records 105. The machine learning system 120 can then identify the action(s) indicated in the event records 105, rather than directly evaluating the motion data.

In some embodiments, the machine learning system 120 generates labeled training data 205 to include (or exclude) various pieces of information, depending on the particular implementation. For example, as discussed above, the machine learning system 120 may prepare some labeled training data 205 that includes only data in the event record 105, such that a model can be trained to generate medical codes for the specific interaction. In some embodiments, the machine learning system 120 may prepare labeled training data 205 that also includes some information from the patient data 110 (such as biographical data, historical data, and the like). This can allow the machine learning system 120 to train a model that considers not only the immediate interaction, but also the broader context of the patient.

In some embodiments, the machine learning system 120 generates labeled training data 205 that includes aggregated data from a number of users. That is, the machine learning system 120 can generate labeled exemplars based on data from any number of patients. In an embodiment, the machine learning system 120 may first anonymize the data to protect the privacy of the patient. By using data from multiple patients, the labeled training data 205 can be used to train a single model, which may then be used to evaluate data from any given patient. Such aggregated training can enable far more accurate models.

In some embodiments, the machine learning system 120 can train a global model using labeled training data 205, and refine the model separately for one or more users or facilities using labeled training data 205 corresponding to those users. That is, for each relevant user (e.g., caregiver) or facility, the machine learning system 120 may refine the global model using data associated with the relevant user (or facility) in order to generate a personalized model. This may enable the machine learning system 120 to retain the accuracy of the global model (achieved using large amounts of data from different users) while also enabling more personalized (and potentially more accurate) predictions for the specific user or facility.

For example, for a given healthcare professional, the machine learning system 120 may use corresponding event records 105 (e.g., records that identify the given healthcare professional as the provider of the services) to refine the global model. During runtime, this personalized model can be used to code the actions of the specific user, which may increase accuracy.

In a related embodiment, the machine learning system 120 may train or refine one or more models based on the payer(s). That is, if the models are being trained to generate medical codes, which can be used to seek payment or reimbursement for medical services, the machine learning system 120 may train or refine a model for each specific payer. For example, the machine learning system 120 may receive prior records (including corresponding codes) that were approved or paid by each payer, and use these records to refine or train a payer-specific model for each such payer. This can allow each model to specialize for the needs or preferences of the payer, improving the probability that the automatically-generated codes will be accepted.

In embodiments, the labeled training data 205 may be stored and used for future training or refinement, as appropriate. In some embodiments, the machine learning system 120 generates the labeled training data 205 continuously (e.g., as new data is received, or whenever a submitted record is approved or paid). For example, in one such embodiment, each time a new event record 105 is recorded or approved, the machine learning system 120 can evaluate it to retrieve the corresponding code, patient data 110, and/or motion data, and generate an exemplar of labeled training data 205. This can allow the machine learning system 120 to continuously update the set of labeled training data 205, such that it is ready for use at any time.

In some embodiments, the machine learning system 120 can alternatively update the labeled training data 205 periodically, or upon some defined criteria or occurrence. For example, the machine learning system 120 may periodically evaluate the event records 105 (e.g., daily, weekly, and the like) to generate labeled training data 205. This may allow the machine learning system 120 to perform the label generating workflow 200 during defined times when the load on the system is low (such as overnight) which can reduce the computational burden on the machine learning system 120, thereby improving its ability to handle other workloads (such as the actual training or inferencing).

Figure 3:
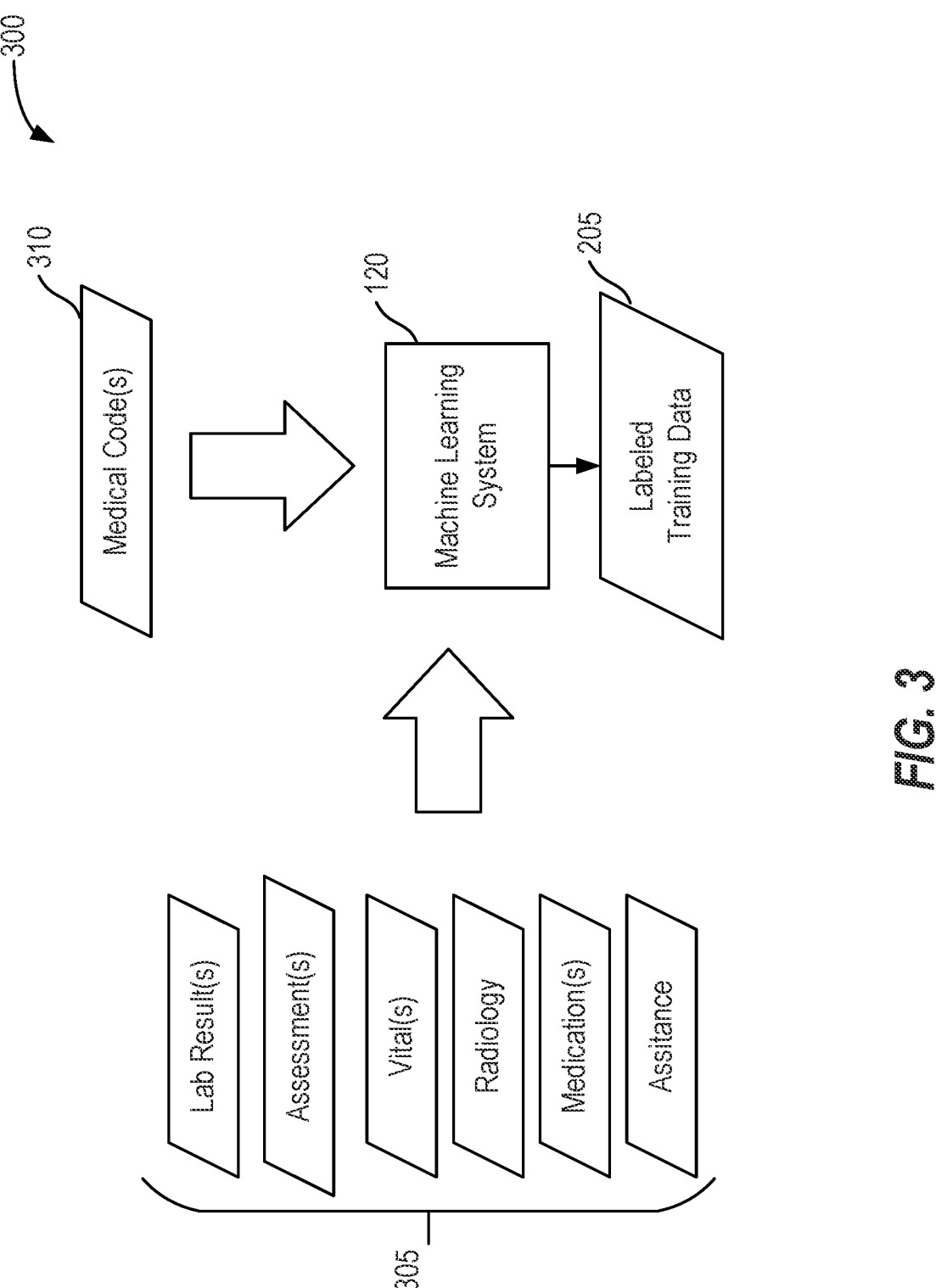
FIG. 3 depicts an example workflow for generating labeled data to train machine learning models to perform coding.

Example Workflow for Generating Labeled Data to Train Machine Learning Models to Perform Coding FIG. 3 depicts an example workflow 300 for generating labeled data to train machine learning models to perform coding. In some embodiments, the workflow 300 provides additional detail for the environment 200 of FIG. 2.

In the illustrated workflow 300, a diverse set of inputs 305 are received, evaluated, and/or aggregated by the machine learning system 120 in order to generate the labeled training data 205. In some embodiments, the inputs 305 are extracted from various sources, such as patient data, event records, and the like. Additionally, as illustrated, the machine learning system 120 also receives or extracts medical codes 310. In embodiments, these medical codes 310 may similarly be extracted from event records, from approved submissions (e.g., reimbursement applications that have been approved, and the like).

In the illustrated example, the inputs 305 include a wide variety of data. The depicted inputs 305 are included as examples for conceptual clarity, and the particular inputs used in various embodiments may differ depending on the particular application. That is, depending on the specific deployment and implementation of the techniques described herein, the machine learning system 120 may evaluate all, a subset of, or none of the depicted inputs 305. Additionally, in some aspects, other inputs may be used depending on the particular problem space and implementation.

In embodiments, the inputs 305 (or the underlying event records and/or patient data) can be stored in any suitable repository (or collection of repositories). For example, in some embodiments, some or all of the inputs 305 may be stored or otherwise available in a Minimum Data Set (MDS) system. As used herein, an MDS system corresponds to a process for clinical assessment of the residents in a residential facility (e.g., a nursing home). In some aspects, MDS systems may be mandated by federal law for any Medicare or Medicaid certified facility. Generally, the MDS system involves a comprehensive and standardized assessment of each resident's functional capabilities and health needs. These assessments may generally be conducted by the facility staff (e.g., trained nursing home clinicians) at various times, including at admission and/or discharge, as well as at other intervals (e.g., quarterly, annually, or when residents experience a significant change in status). In some embodiments, the MDS can generally capture information about the comorbidities of each resident, physical, psychological and psychosocial functioning of each resident, any treatments (e.g., hospice care, oxygen therapy, chemotherapy, dialysis) or therapies (e.g., physical, occupational, speech, restorative nursing) received by each resident, and the like.

In the illustrated example, the inputs 305 include "lab results," "assessments," "vitals," "radiology," "medications," and "assistance," each of which is discussed in more detail below, in turn.

In one embodiment, the "lab results" input 305 corresponds to the results of any medical lab tests that were prepared for the patient, such as blood tests (e.g., indicating cholesterol levels), biopsies, and the like. In some embodiments, the lab results input 305 includes tests that were completed in association with a given interaction event. For example, the lab results may identify labs that were ordered and/or performed during a given interaction, the results from any labs that were ordered during the interaction, results that were received and/or evaluated during the interaction (e.g., when the healthcare provider discussed the results of a prior test with the patient), and the like. Generally, the lab tests that were ordered, as well as the results of lab tests, may be useful in predicting the proper medical codes for the interaction.

In some embodiments, the "assessments" input 305 includes information relating to clinical assessments or notes prepared by the healthcare provider. For example, a nurse, clinician, doctor, or other caregiver may prepare natural language narratives describing the interaction, such as the reason for the visit, the symptoms presented, suspected diagnoses, and the like. In some embodiments, these notes are processed using one more natural language processing (NLP) techniques, such as to identify keywords, extract features of the text, generate a vector representation, and the like. This extracted and/or vectorized data can then be used as an input feature to the machine learning system 120. In embodiments, these assessments (and the terminology used) can be particularly useful in predicting accurate medical codes.

In one embodiment, the "vitals" input 305 includes information relating to vitals of the patient, such as their age, weight, height, and the like. In some embodiments, the vitals input 305 include the vitals of the patient at the time of the interaction or intervention. For example, the vitals may indicate the patient's height and weight during a scheduled appointment. In some embodiments, the vitals input 305 also includes trends in the patient's vitals, such as whether their weight is trending up or down, whether their blood pressure or pulse rate is steady, and the like.

In an embodiment, the "radiology" input 305 includes information relating to radiology results for the patient, including diagnostic radiology and interventional radiology. The radiology input 305 can generally correspond to the results of imaging scans, such as using x-ray, ultrasound, CT scans, and the like. In some embodiments, in a similar manner to the lab results input 305, the radiology input 305 can include not only indications of the imaging that was scheduled at a given interaction event, but also the results of any prior imaging (e.g., diagnoses or other results, as indicated by the healthcare provider).

In one embodiment, the "medications" input 305 includes information relating to the current, past, or prescribed medication(s) used by the patient. In some embodiments, this input 305 specifically indicates any medications that were newly prescribed during a given interaction, and/or medications that were terminated at the interaction (e.g., where a doctor told the patient to stop using a medication). In some embodiments, in addition to or instead of indicating specific medications, this medication input 305 can indicate the type of the medication(s). For example, the input may indicate whether each medication corresponds to a generic or over-the-counter medication such as ibuprofen, if it involves administration of a psychotropic drug or some other controlled substance (such as opioids), or whether it requires additional skill or time, such as an intravenous (IV) medication, and the like.

In an embodiment, the "assistance" input 305 includes information relating to other actions or assistance provided to the patient during the interaction event (or prior events). For example, as discussed above, in some embodiments the machine learning system 120 can determine the actions performed (e.g., using motion data for the healthcare provider), and include these determined actions. In some embodiments, the machine learning system 120 can additionally or alternatively identify other action(s) specified or indicated by the user.

As discussed above, in some embodiments, there may be other inputs used by the machine learning system 120. For example, in one such embodiment, the input 305 can more broadly include diagnoses of the patient.

In the illustrated workflow 300, the machine learning system 120 receives this input 305 (and possibly other data) to generate a set of input data for training the model. For example, the machine learning system 120 can aggregate the information into one or more vectors to be used as input to predict appropriate medical code(s). In some aspects, as discussed above, the machine learning system 120 can anonymize the input 305 in various ways. For example, rather than specifically identifying the patient(s), the machine learning system 120 may anonymize the data, as discussed above, in order to allow the model(s) to be trained without compromising the patient's privacy. This can allow the machine learning system 120 to learn how to accurately generate medical codes, without exposing the underlying resident data.

In the illustrated embodiment, the label used as target output for the labeled training data 205 is the medical code(s) 310 that are associated with the interactions. In an embodiment, as discussed above, healthcare providers can generally assign these codes to the interaction event(s) to indicate the actions performed, diagnoses, reason for the visit, and the like. In one such embodiment, the data associated with each interaction (e.g., the labs ordered during the visit, the results discussed during the visit, the actions performed, and the like) can be labeled with the medical code(s) 310 selected by the user.

As discussed below in more detail, these labeled training data 205 can then be used to train and/or refine one or more machine learning models, allowing the machine learning system 120 to automatically generate medical codes for any interaction event, given a set of relevant data associated with the event.

Figure 4:
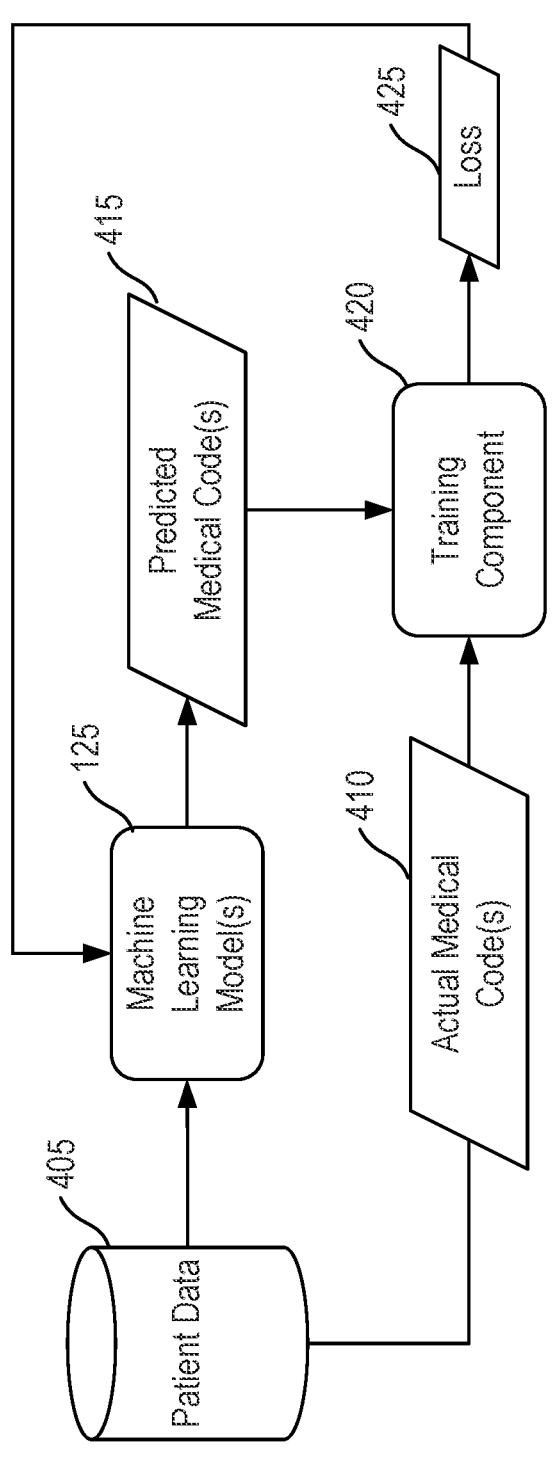
FIG. 4 depicts an example workflow for iteratively refining machine learning models to perform medical coding.
Figure 4:

Example Workflow for Iteratively Refining Machine Learning Models to Perform Medical Coding FIG. 4 depicts an example workflow 400 for iteratively refining machine learning models to perform medical coding. In some embodiments, the workflow 400 is performed by a machine learning system, such as machine learning system 120 of FIG. 1.

As illustrated, the workflow 400 begins with patient data 405 as input. In some embodiments, as discussed above, the patient data 405 can generally include biographical or demographic data for one or more patient(s), as well as one or more event records including information relating to interactions between the patient(s) and one or more users (e.g., healthcare providers). For example, for a given patient, the patient data 405 may include not only the patient's biographical data such as age, height, and weight, but also a sequence of event records, each indicating the relevant data from a corresponding interaction (e.g., lab results at the time, medications prescribed at the time, and the like).

As illustrated, the machine learning system can process some or all of the patient data 405 using the machine learning models 125 in order to generate a set of one or more predicted medical codes 415. In some embodiments, as discussed above, the machine learning system may process the data associated with each interaction event separately. That is, the machine learning system may generate predicted medical codes 415 for each respective interaction event by processing data associated with the respective event using the machine learning models 125.

For example, if one event in the patient data 405 corresponds to a routine checkup, the machine learning system may process the associated data (e.g., the vitals that are recorded, the assessments written by the provider, any noted issues or concerns, and the like) using the machine learning models 125 in order to generate one or more predicted medical codes 415 for the specific checkup.

As illustrated, the machine learning system can also extract the actual medical codes 410 for each event. That is, for each event (used to generate a corresponding predicted medical code 415), the machine learning system can also determine the actual medical codes 410 that were assigned to the event (e.g., by the assisting physician).

As illustrated, the predicted medical codes 415 and actual medical codes 410 can be provided to a training component 420, which generates a loss 425 based on the input codes. In embodiments, the particular algorithm or formulation of the loss 425 may differ depending on the particular implementation. For example, the machine learning system may use cross-entropy loss, hinge loss, and the like.

In some embodiments, the machine learning system generates a separate loss 425 for each training exemplar (e.g., for each interaction event, or for each medical code). For example, using stochastic gradient descent, the machine learning system can generate a separate loss 425 for each such event, and refine the model separately for each such event. In some embodiments, the machine learning system can use batch gradient descent, such as by generating an overall loss 425 based on a number of exemplars (e.g., across multiple events), and update the models based on this aggregated batch loss.

As illustrated, the machine learning system can use the loss 425 to refine the machine learning models 125. For example, using backpropagation, the machine learning system can compute a set of gradients based on the loss 425 and the weights or parameters of the final layer of a neural network model. These gradients can be used to refine these weights, and then be backpropagated towards the first layer of the model, performing similar refinement at each layer.

In some embodiments, as discussed above, the machine learning system may initialize the machine learning models 125 using random parameters. That is, the machine learning system may randomly set weights, biases, or other parameters of the model. As a result, the predicted medical codes 415 at early stages of training will tend to be relatively inaccurate (and often fairly random). However, using the workflow 400, the machine learning system can iteratively refine these parameters based on the losses 425. This allows the machine learning models 125 to learn to generate more accurate predicted medical codes 415 during runtime.

Example Workflow for Using Machine Learning to Perform Medical Coding

Figure 5:
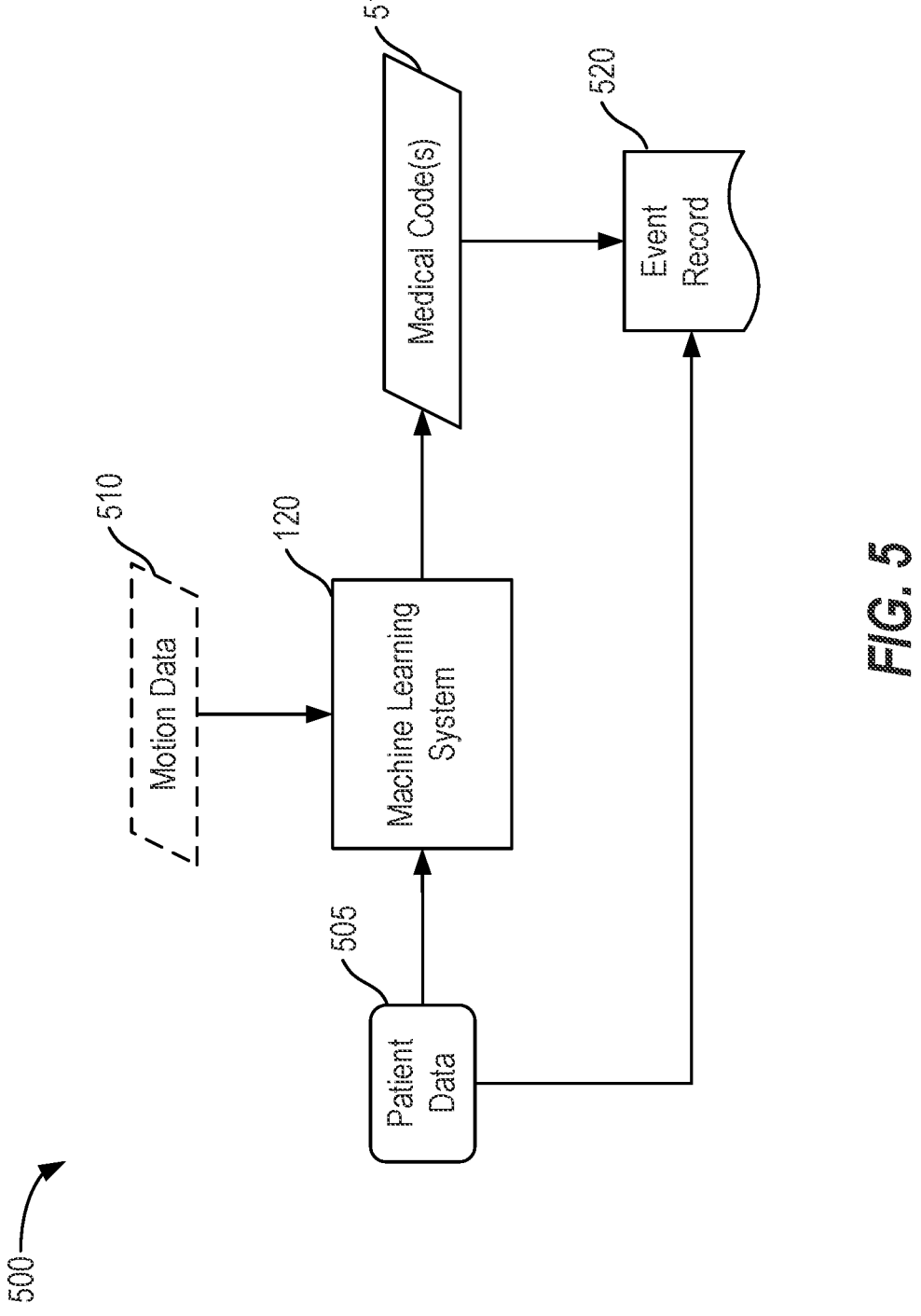
FIG. 5 depicts an example workflow for using machine learning model to perform medical coding.

FIG. 5 depicts an example workflow 500 for using machine learning to perform medical coding. In one embodiment, in the workflow 500, the machine learning system 120 uses a set of trained machine learning models (e.g., the machine learning models 125 of FIG. 1) to process and classify patient data during runtime.

In some embodiments, as discussed above, the machine learning system 120 can both train the models, as well as use them for inferencing during runtime. In other aspects, the machine learning system 120 may receive and use models trained by one or more other components. In still another embodiment, the machine learning system 120 may train the models, and deploy them to one or more other systems for inferencing.

The illustrated workflow 500 corresponds to use of the models during an inferencing stage. As used herein, "inferencing" generally refers to the phase of machine learning where the model(s) have been trained, and are deployed to make predictions during runtime. As illustrated, during inferencing, the machine learning system 120 receives patient data 505 from one or more repositories. In some embodiments, as illustrated, the machine learning system 120 can optionally receive and evaluate motion data 510, as discussed above.

In some embodiments, the machine learning system 120 receives this patient data 505 and/or motion data 510 in real-time (or near real-time). That is, the machine learning system 120 may receive and evaluate the data during or shortly after a given interaction event. For example, when a user indicates that an event has finished (e.g., a scheduled appointment is over), the machine learning system 120 can retrieve or receive the corresponding patient data 505 from the event (as well as the motion data 510 from the user during the event, in some aspects).

The machine learning system 120 may generally process the patient data 505 and/or motion data 510 using one or more trained machine learning models to generate appropriate medical codes (e.g., ICD-10 codes) indicating the relevant diagnoses, reasons for visit, and the like. In some embodiments, as discussed above, generating these codes can include processing the data using multiple models. For example, the machine learning system 120 may use a first model to process patient data 505, and a second model to process the motion data 510. In some embodiments, the machine learning system 120 can use different models for each subset of the patient data 505. For example, a first model may be trained to generate medical codes based on written assessments, while a second is used to generate codes based on lab results. This may allow the models to learn for the specific features relevant to each type of input, enabling more accurate code generation.

In some embodiments, as discussed above, the machine learning system 120 may use a global model (shared across users and/or facilities) to classify the motion data 510 and/or generate medical codes 515. In other embodiments, the machine learning system 120 may use user-specific or facility-specific models (trained or refined based on data from a single user, or a set of users) to classify the data.

In some embodiments, the trained model(s) generate probability scores for each code, and the machine learning system 120 can identify the medical code 515 having the highest score. In at least one embodiment, the machine learning system 120 can identify any output codes having a score that exceeds some threshold, and output this set as the medical codes 515.

As illustrated, the machine learning system 120 can then use the generated medical code(s) 515 for the interaction, in conjunction with the patient data 505, to generate a corresponding event record 520 for the interaction. For example, if the machine learning system 120 processed all or a subset of a newly-created record to generate the medical codes 515, the machine learning system 120 can then associate, add, or otherwise link the event record 520 with the generated medical codes 515. In this way, the machine learning system 120 can automatically generate complete event records 520, including appropriate medical codes 515, without requiring that the user manually do so.

In at least one embodiment, prior to finalizing the event record 520, the machine learning system 120 can first verify its contents based on a variety of criteria. For example, the machine learning system 120 may confirm that the predicted medical codes 515 are associated with a confidence value that meets a defined threshold. That is, if the machine learning model outputs a confidence in its prediction, the machine learning system 120 can confirm that the confidence exceeds a minimum value. If not, the machine learning system 120 may flag the event record 520 as unverified (or refrain from creating it entirely).

In one embodiments, the machine learning system 120 can verify the record by evaluating various patient data. In one such embodiment, the machine learning system 120 may confirm that the generated medical codes 515 are plausible for the specific patient. For example, if the patient data 505 indicates that the patient previously had their left arm amputated, but the medical code 515 relates to the left hand (e.g., M79.645, pain in left finger(s)), the machine learning system 120 may determine that the code is likely inaccurate. In response, the system may suggest an alternative code (e.g., M79.644, pain in right finger(s)), flag the event record 520 as unverified, or refrain from creating it.

In some embodiments, the machine learning system 120 can cause some or all of the event records 520 to be manually reviewed and verified, prior to finalizing them. For example, the machine learning system 120 may identify the user (e.g., healthcare provider) associated with the interaction, and transmit the event record 520 (or only the medical codes 515) to this user for approval. In some aspects, this approval process is used for all event records 520. In one embodiment, the machine learning system 120 only seeks approval during an initial testing stage of deployment (e.g., after the models are trained but before they have been in use and confirmed to be accurate). Once the model(s) are confirmed to be mature, in such an embodiment, the machine learning system 120 can cease the approval process.

In some embodiments, the machine learning system 120 may randomly select a subset of the event records 520 for approval, in order to confirm that the model(s) are functioning accurately. Further, in some embodiments, the machine learning system 120 may prompt for approval only when various conditions are met (such as minimum confidence, conflicting patient data, and the like), as discussed above.

Though some embodiments may therefore still involve manual approval, the machine learning system 120 is nevertheless able to significantly reduce manual effort in the coding process. For example, because the machine learning system 120 can automatically select appropriate medical codes 515 (from a defined list that may include several tens of thousands of alternatives), the user need not enter it. In some embodiments, even if the medical codes 515 cannot be determined with sufficient confidence, the machine learning system 120 may offer a relatively small set of alternatives, allowing the user to quickly select the correct one(s).

Though the illustrated example depicts the machine learning system 120 performing inferencing, in some embodiments, as discussed above, training and inferencing may be performed on separate systems. For example, a centralized system may train the models (e.g., using data from multiple users and/or multiple facilities), and the models may be distributed to each local facility for inferencing by local system(s).

Example Workflow for Using Machine Learning to Diagnose and Treat Patients

Figure 6:
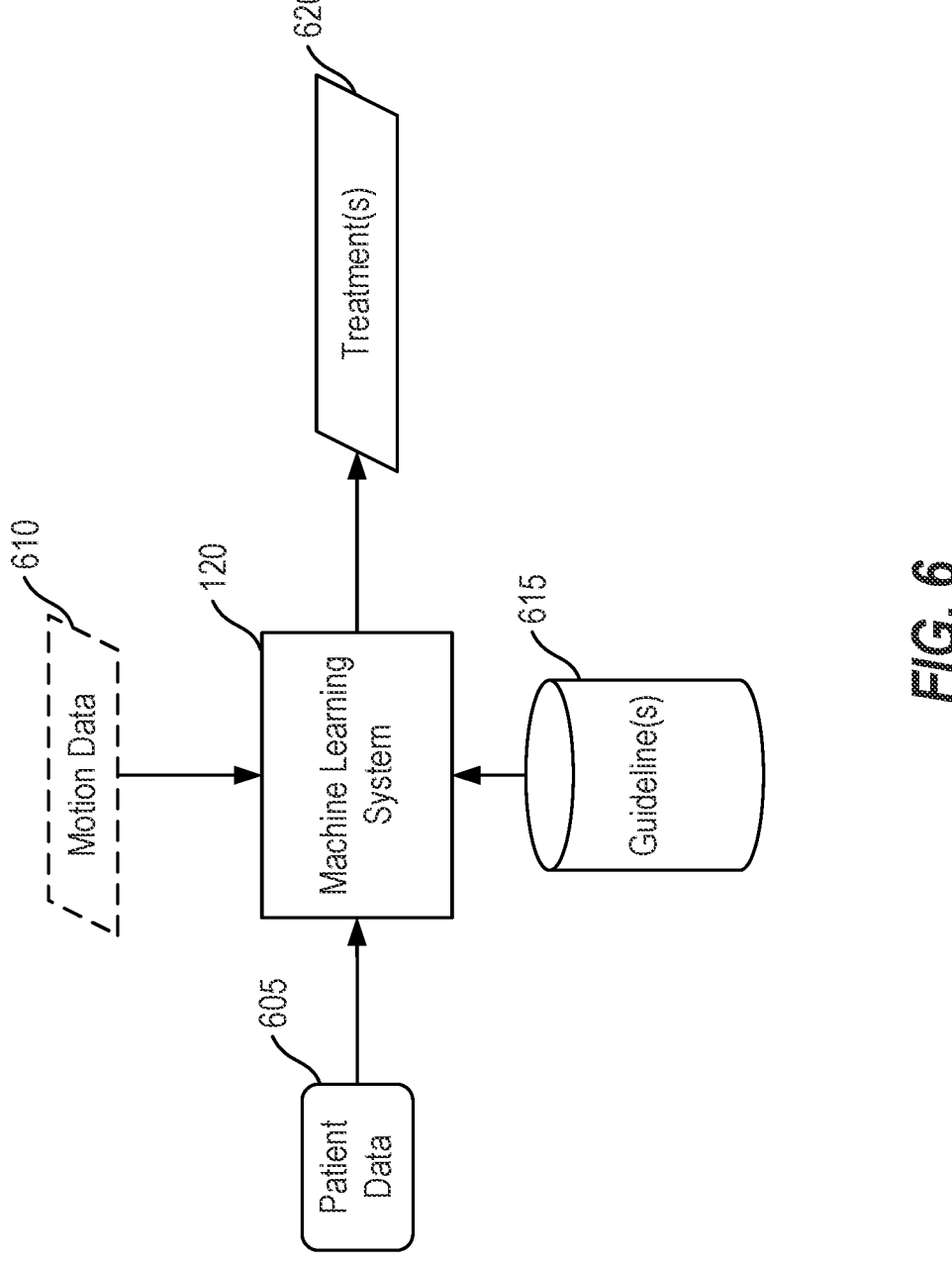
FIG. 6 depicts an example workflow for using machine learning to diagnose and treat patients.

FIG. 6 depicts an example workflow 600 for using machine learning to diagnose and treat patients. In one embodiment, in the workflow 600, the machine learning system 120 uses a set of trained machine learning models (e.g., the machine learning models 125 of FIG. 1) to process and classify patient data during runtime, in order to drive diagnosis and treatment decisions.

In some embodiments, the workflow 600 is performed alongside or subsequent to the workflow 500 of FIG. 5. For example, as discussed above with reference to the workflow 500, the machine learning system 120 may receive patient data 605 and/or motion data 610 during or shortly after a given interaction event. For example, when a user indicates that an event has finished (e.g., a scheduled appointment is over), the machine learning system 120 can retrieve or receive the corresponding patient data 605 from the event (as well as the motion data 610 from the user during the event, in some aspects).

As discussed above, the machine learning system 120 may generally process the patient data 605 and/or motion data 610 using one or more trained machine learning models to generate appropriate medical codes (e.g., ICD-10 codes) indicating the relevant diagnoses, reasons for visit, and the like. In some embodiments, the machine learning system 120 can further generate or supplement the corresponding event records for the interaction.

In the illustrated example, the machine learning system 120 can then further use these event records and/or generated medical codes in order to diagnose the patient, and/or to generate one or more treatments 620. In one such embodiment, the machine learning system 120 can identify the medical issue(s) reflected in the generated code. The machine learning system 120 can then evaluate the patient data 605 (including not only data from the current event, but also from prior interactions) in order to determine whether the issue has been diagnosed.

For example, suppose the machine learning system 120 generated a medical code T84.610A (infection and inflammatory reaction due to internal fixation device of right humerus, initial encounter), or some more generic infection code, based on a most-recent interaction with the patient. In the workflow 600, the machine learning system 120 may evaluate the patient data 605 to determine whether the patient has been diagnosed with an infection (e.g., noted in the clinical assessment, indicated by a new prescription for antibiotics, and the like). If the machine learning system 120 determines that the infection has not been recognized, the machine learning system 120 may take a variety of actions.

In one embodiment, the machine learning system 120 can output the medical code and/or issue to the user, prompting them to confirm or investigate. In at least one embodiment, the machine learning system 120 can enter a relevant diagnosis in the patient data 605, and/or select one or more treatments 620. In the illustrated example, the machine learning system 120 may parse guidelines 615 to determine proper treatments 620.

The guidelines 615 generally include medical guidance with respect to the proper treatment(s) for a variety of disorders and issues. For example, the guidelines 615 may indicate which antibiotics are appropriate for given types of infection, as well as what characteristics the patient should have to ensure the proper antibiotic is selected. In an embodiment, the machine learning system 120 can parse the guidelines 615 in view of the generated medical code and/or patient data 605 to identify the proper course. The machine learning system 120 can then output this as a suggested or indicated treatment 620.

In this way, the machine learning system 120 is able to recognize medical issues that may have gone unnoticed by the user(s). For example, based on its trained models, the machine learning system 120 may determine or infer that the user has an infection before the doctor even realizes it. This personalized and targeted diagnostic approach can enable significantly improved care.

Additionally, by evaluating the guidelines 615, the machine learning system 120 may be able to quickly and efficiently provide suggested treatments 620, allowing the user (e.g., the doctor) to review and approve the plan efficiently. In this way, the patient receives significantly improved and personalized care.

Example Method for Training Machine Learning Models to Perform Coding

Figure 7:
FIG. 7 is a flow diagram depicting an example method for training machine learning models to perform coding.
Figure 7:
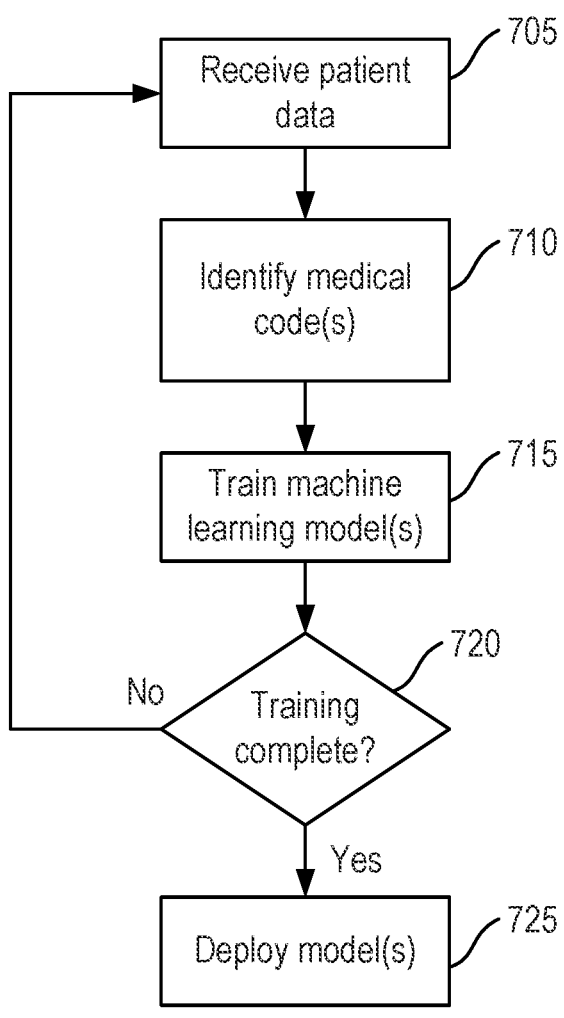

FIG. 7 is a flow diagram depicting an example method 700 for training machine learning models to perform coding. In some embodiments, the method 700 is performed by a machine learning system, such as machine learning system 120 of FIG. 1.

At block 705, the machine learning system receives patient data. As discussed above, this patient data may generally be indicative of various characteristics of the patient and/or information related to one or more interactions between the patient and a healthcare provider. For example, the patient data may correspond to an event record generated by a user during or after a medical visit. As discussed above with reference to FIG. 3, the data may include a variety of relevant data such as lab results, assessments, vitals, radiology results, medications, and the like.

In one embodiment, the patient data corresponds to a single interaction event for a single patient. That is, the machine learning system may receive and process each event as a discrete training exemplar (e.g., using stochastic gradient descent). In other embodiments, the patient data may include multiple events, reflecting interactions with one or more patients. This may allow the machine learning system to process the events in batches (e.g., using batch gradient descent).

At block 710, the machine learning system can identify the medical code(s) that were assigned (e.g., by the assisting physician) to the patient data (e.g., to the event record(s)). As discussed above, in conventional systems, users generally select and assign medical codes to reflect what occurred during the interaction. In some aspects, these codes are used (or required) for billing purposes. Additionally, in some embodiments, other non-assisting users (e.g., reviewers) can review generated records to ensure that the assisting user(s) selected the proper code(s). In some embodiments, as discussed above, the medical code(s) include ICD codes, such as using ICD-10-CM.

At block 715, once the patient data and corresponding code(s) have been determined, the machine learning system trains one or more machine learning models based on the labeled data. One example technique for training the machine learning model(s) is described in more detail below with reference to FIG. 9.

In some embodiments, the machine learning system trains a single model to classify the data. That is, a single model may be trained to receive and classify all patient data in order to predict proper medical code(s). In other embodiments, separate models may be used for various portions of the input data. For example, a first model may be used to generate code(s) based on written assessments, while a second processes lab result(s) and a third classifies user action(s) (e.g., based on motion data).

In one embodiment, the machine learning system trains a global model to generate the predicted code(s). In some embodiments, as discussed above, the machine learning system may train (or refine) separate models for each user and/or each facility. For example, at block 715, the machine learning system may select the model that corresponds to the specific user associated with the event data (e.g., the caregiver who entered the assessment), and refine this model. Similarly, if a model is shared across a facility or geographic area (which may enable the machine learning system to specialize for the specific preferences and practices of the given area), the machine learning system can select and refine this specific model.

In some embodiments, if the medical code involves a hierarchical structure, the machine learning system may train one or more models at each level of the structure. For example, the machine learning system may train a first model for an initial level (e.g., to classify the patient data as relating to diseases of the immune system, diseases of the nervous system, diseases of the skin, and the like). Within each such category, one or more further models can be trained to further classify the input patient data into the relevant subcategories, until a final model generates an output medical code at the lowest level of the hierarchical structure.

Generally, during the training process, the model(s) can be iteratively refined to produce more accurate medical codes. In some embodiments, the models may be initialized using random parameters, resulting in effectively random classifications. However, as these parameters are refined over time using labeled data (as discussed above and below in more detail), they can generally learn to generate accurate codes for the data.

As discussed above, although the illustrated method 700 depicts training the model individually for each action, in some embodiments, the machine learning system may train the model for batches of data. For example, using stochastic gradient descent, the machine learning system may compute a loss based on a single event record and medical code pair, and refine the model using this loss. Using batch gradient descent, the machine learning system may compute a loss based on a batch of events and corresponding codes, refining the model based on this batch of data.

At block 720, the machine learning system determines whether training is complete. In embodiments, this can include evaluation of a wide variety of termination criteria. For example, in one embodiment, the machine learning system can determine whether training is complete based on whether there is any additional training data available. If at least one exemplar (e.g., at least one event record that has not yet been used to train the model(s)) remains, the method 700 may return to block 705. In some embodiments, the machine learning system can additionally or alternatively determine whether a maximum amount of time, a maximum number of training cycles or epochs, and/or a maximum amount of computing resources have been spent training the model(s). If not, the method 700 returns to block 705.

In at least one embodiment, to determine whether training is complete, the machine learning system can determine whether the model(s) have reached some preferred minimum accuracy. For example, using a set of testing data (e.g., patient data, labeled with the corresponding medical codes, that has not been used to train the model), the machine learning system can test the accuracy of the predictions (such as by processing the patient data using the model(s), and determining how often the output codes matches the actual medical codes used). If the model accuracy is still not satisfactory, the method 700 returns to block 705.

Regardless of the specific termination criteria used, once the machine learning system determines that training is complete, the method 700 continues to block 725, where the machine learning system deploys the trained model(s) for runtime. In some embodiments, as discussed above, the machine learning system can use the model(s) locally to perform inferencing. That is, the machine learning system may be used to both train the models, as well as use them to classify patient data during runtime. In some embodiments, the machine learning system may additionally or alternatively provide the models to one or more other systems that perform runtime inferencing.

Figure 8:
FIG. 8 is a flow diagram depicting an example method for generating labeled training data to train machine learning models to perform coding.
Figure 8:
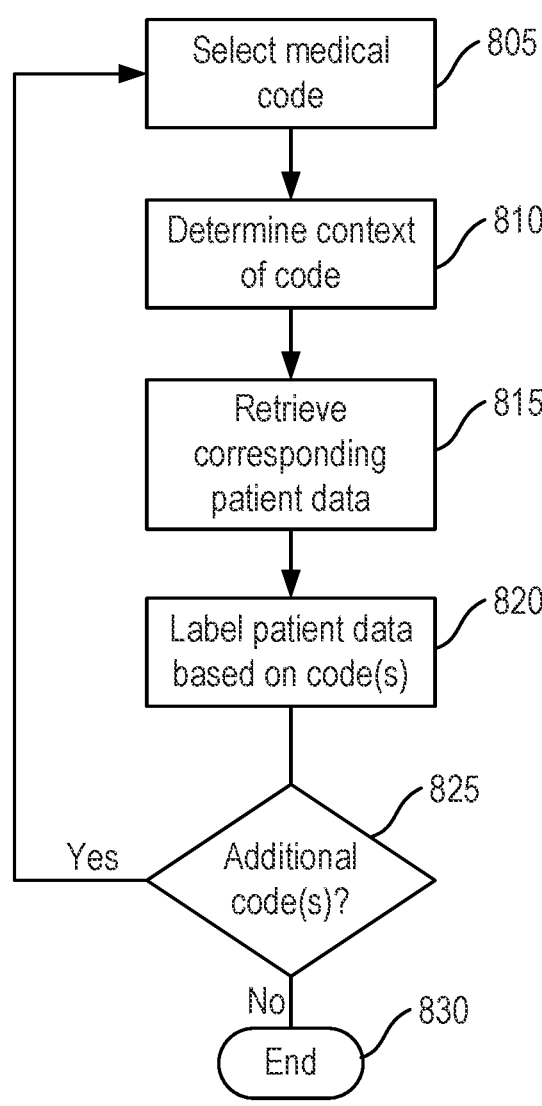

Example Method for Generating Labeled Training Data to Train Machine Learning Models to Perform Coding FIG. 8 is a flow diagram depicting an example method 800 for generating labeled training data to train machine learning models to perform coding. In some embodiments, the method 800 is performed by a machine learning system, such as machine learning system 120 of FIG. 1. In one embodiment, the method 800 provides additional detail for blocks 705 and/or 710 of FIG. 7, where the machine learning system correlates patient data and medical codes.

At block 805, the machine learning system selects a medical code reflected in patient data. That is, the machine learning system may identify a medical code that was used to label one or more interactions with a patient. In an embodiment, the machine learning system may use any suitable criteria or technique to select the medical code at block 805, as all of the assigned codes will be similarly evaluated during the labeling process. Though the illustrated example depicts a sequential process (iteratively evaluating each code in turn) for conceptual clarity, in some embodiments, the machine learning system can evaluate some or all of the codes entirely or partially in parallel.

At block 810, the machine learning system determines the context of the selected medical code. In embodiments, the context may include a variety of detail, such as the time when the code was recorded or selected, the date of the interaction, the user that selected the medical code, and the like. In some embodiments, the immediate context of the code corresponds to the event record to which the code was assigned. For example, as discussed above, the patient data may include a sequence of interaction event records, each indicating relevant data for the time the event occurred. In one such embodiment, at block 810, the machine learning system can identify this record and determine the relevant context of the interaction, such as when it occurred, who the patient was, the purpose and/or result of the interaction, and the like.

At block 815, based on this contextual data, the machine learning system can retrieve additional patient data, if it exists. For example, the machine learning system may determine the patient's age, prior diagnoses (which may not be reflected in the current event record), prior medications, and the like.

Once the corresponding patient data for the code has been identified, the method 800 continues to block 820, where the machine learning system labels the patient data based on the selected medical code. That is, the machine learning system can generate a training exemplar including the patient data (e.g., the data associated with the specific interaction and/or data about the corresponding patient, in general) as the input data, and the selected medical code as the target output for the input.

Though the illustrated example depicts identifying relevant patient data for a given medical code, in some embodiments, the machine learning system may additionally or alternatively identify relevant medical code(s) for given patient data. That is, the machine learning system may select an event record, and identify the medical code(s) that were assigned to the record.

The method 800 then continues to block 825, where the machine learning system determines whether there are any additional medical codes that are reflected in the patient data but that have not yet been used to generate a labeled exemplar. If so, the method 800 returns to block 805. If not, the method 800 terminates at block 830.

Example Method for Refining Machine Learning Models to Perform Coding

Figure 9:
FIG. 9 is a flow diagram depicting an example method for refining machine learning models to perform coding.
Figure 9:
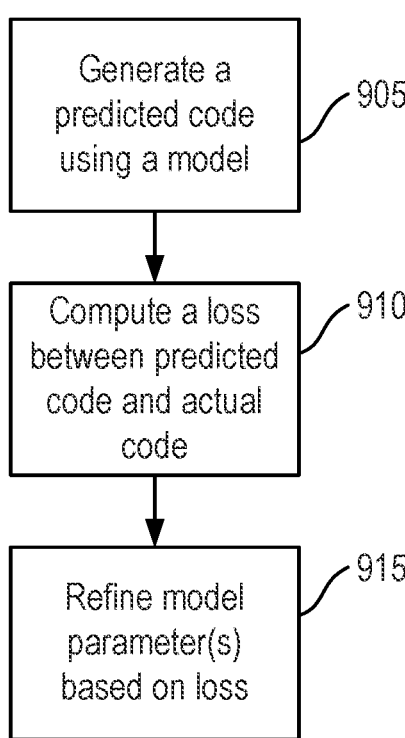

FIG. 9 is a flow diagram depicting an example method for refining machine learning models to perform coding. In some embodiments, the method 900 is performed by a machine learning system, such as machine learning system 120 of FIG. 1. In one embodiment, the method 900 provides additional detail for block 715 of FIG. 7, where the machine learning system trains the machine learning model(s).

At block 905, the machine learning system generates a predicted medical code by processing patient data using a machine learning model. For example, as discussed above, the machine learning system may generally evaluate the patient data (e.g., an event record) to extract data associated with a given interaction (such as lab results). In some embodiments, as part of generating the predicted code, the machine learning system can perform one or more preprocessing operation son the data, such as to vectorize it.

At block 910, the machine learning system computes a loss between the predicted medical code (generated at block 905) and an actual ground-truth medical code for the patient data that was used to generate the predicted medical code (e.g., indicated in a label, and/or extracted from the event record).

In at least one embodiment, the actual model output (or the output at a penultimate layer of the model) is a set of scores, one for each class (e.g., for each possible medical code), and the predicted code is selected by identifying the output(s) with the highest score(s). In one such embodiment, to generate the loss, the machine learning system can use various loss algorithms that seek to maximize the score(s) of the "correct" class(es) while minimizing the scores of the "incorrect" classes, such as hinge loss, cross entropy loss, and the like.

At block 915, the machine learning system can then refine the parameters (e.g., weights and/or biases) of the model based on the loss generated in block 910. In this way, after the refinement, the model would generate a somewhat different output (e.g., a different predicted code, or different score(s) for the possible codes) if it processed the same input. After a number of training rounds and/or epochs, the model thereby learns to accurately classify the input data.

Although a single machine learning model is depicted in the method 900, in some embodiments, the machine learning system can use multiple models. For example, a first model may be trained to generate codes based on written assessments, while a second is trained to generate codes based on lab results.

Example Method for Performing Medical Coding Using Machine Learning

Figure 10:
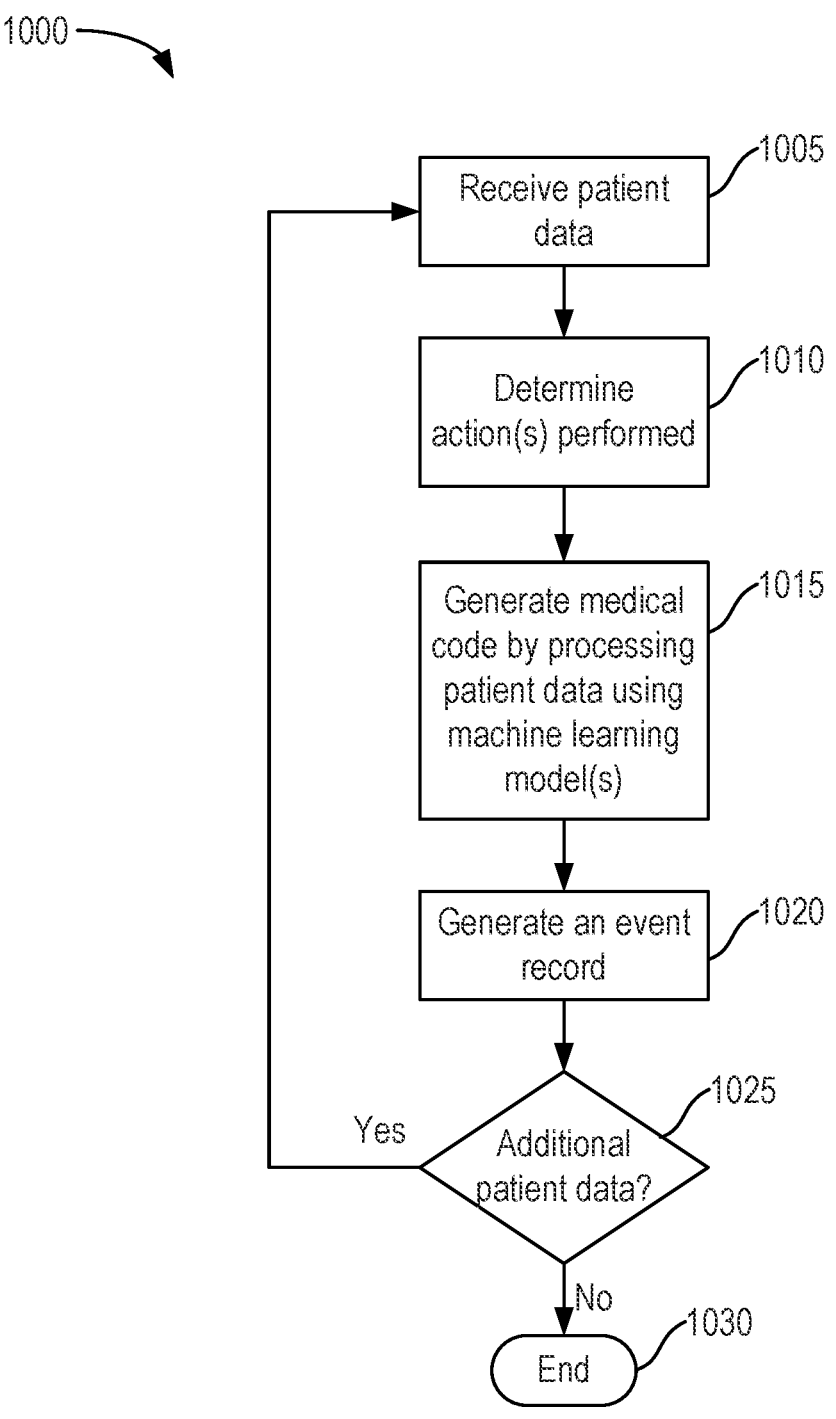
FIG. 10 is a flow diagram depicting an example method for performing medical coding using machine learning.

FIG. 10 is a flow diagram depicting an example method 1000 for performing medical coding using machine learning. In some embodiments, the method 1000 is performed by a machine learning system, such as machine learning system 120 of FIG. 1.

At block 1005, the machine learning system receives patient data for a given patient. In an embodiment, this patient data can generally correspond to data related to an event (e.g., an interaction between the patient and a caregiver). For example, before, during, or after an appointment, the caregiver may prepare the event record to indicate the reason for the visit, the action(s) performed, and the like. In some embodiments, some or all of the event record may be automatically generated. For example, one or more other systems may process motion data to classify the action(s), as discussed above. In an embodiment, the event data is then transmitted to the machine learning system for machine learning-based coding, in order to enable automated coding and review of the event record.

In some embodiments, as discussed above, the patient data may be transmitted to the machine learning system continuously (e.g., as soon as the interaction is over), or may be transmitted during windows and/or in batches. For example, each night, the machine learning system may receive all patient data associated with events that occurred that day. The machine learning system can then process and code this data overnight, allowing it to use resources when the load on the system is otherwise light.

At block 1010, the machine learning system determines one or more actions that were performed in the course of the interaction. For example, as discussed above, the machine learning system (or another system) may receive motion data (e.g., from wrist-mounted sensors on the caregiver), and classify it to indicate what action(s) were performed. In some embodiments, at block 1010, the machine learning system evaluates the patient data to determine what specific actions were recorded or indicated.

At block 1015, the machine learning system generates a predicted medical code for the interaction by processing the patient data and/or action data using one or more machine learning models. In some embodiments, as discussed above, the machine learning system may use a different set of one or more models, depending on the particular user or facility associated with the patient data (e.g., the caregiver that was involved in the interaction). For example, in one embodiment, the machine learning system uses user-specific models that were trained or fine-tuned specifically for the individual user.

In some embodiments, if the medical code involves a hierarchical structure, the machine learning system may use one or more models at each level of the structure. For example, the machine learning system may train and use a first model for an initial level (e.g., to classify the patient data as relating to diseases of the immune system, diseases of the nervous system, diseases of the skin, and the like). Within each such category, one or more further models can be retrieved and used to further classify the input patient data into the relevant subcategories, until a final model generates an output medical code at the lowest level of the hierarchical structure.

At block 1020, the machine learning system generates an event record reflecting the action(s), relevant patient, any associated patient data, and the generated medical code(s). In at least one embodiment, prior to, during, or after generating the event record, the machine learning system can verify or validate the information in it. For example, as discussed above, the machine learning system may evaluate the medical code in view of one or more records of the relevant patient. In one such embodiment, the machine learning system may determine whether the patient records indicate that the medical code is potentially applicable to the relevant patient. For example, if the generated code is K35.80 (indicating unspecific acute appendicitis), the machine learning system may determine whether the patient has already had an appendectomy.

In an embodiment, if the machine learning system fails to validate or verify the record, it can be provided to a user (e.g., the caregiver that participated in the interaction) for verification or correction. In some embodiments, as discussed above, the machine learning system may fail to verify the record because some aspects of it conflict with other data. In at least one embodiment, as discussed above, the machine learning system may also fail to verify a record if it is incomplete (e.g., because the machine learning system could not generate a medical code with sufficient confidence).

At block 1025, the machine learning system determines whether there is any additional patient data that has not yet been evaluated. For example, the received patient data (at block 1005) may include multiple interaction events (e.g., corresponding to multiple actions performed to assist the same patient, or to multiple actions for multiple patients).

If no additional data remains, the method 1000 terminates at block 1030. If the patient data includes at least some set of data that has not yet been evaluated, the method 1000 returns to block 1010.

Figure 11:
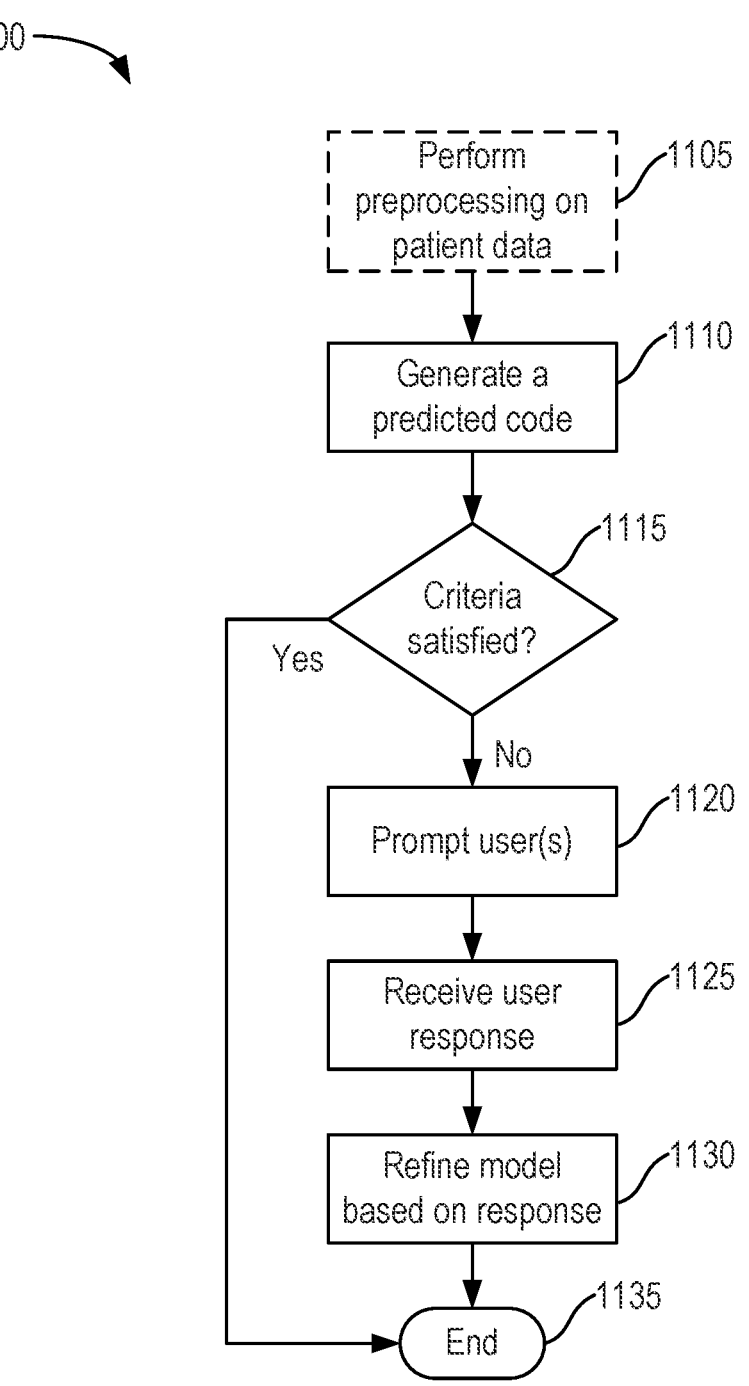
FIG. 11 is a flow diagram depicting an example method for testing and refining machine learning models used to perform medical coding.

Example Method for Testing and Refining Machine Learning Models used to Perform Medical Coding FIG. 11 is a flow diagram depicting an example method 1100 for testing and refining machine learning models used to perform medical coding. In some embodiments, the method 1100 is performed by a machine learning system, such as machine learning system 120 of FIG. 1. In one embodiment, the method 1100 provides additional detail for block 1015 of FIG. 10, where the machine learning system generates a predicted medical code using machine learning model(s).

At block 1105, the machine learning system can optionally perform any needed preprocessing on received patient data. For example, as discussed above, the machine learning system may delineate the data into windows or segments corresponding to interaction events. In some aspects, the machine learning system may extract the relevant subsections from the patient data (e.g., the specific inputs used by the models), and/or prepare this data for processing (e.g., by generating a vector representation of it). Generally, the preprocessing performed in block 1105 can include a wide variety of operations depending on the particular implementation.

At block 1110, the machine learning system generates a predicted code using the patient data. For example, as discussed above, the machine learning system may generate the predicted code by processing all or a subset of the patient data using one or more models that have been trained to generate medical codes to reflect the context and content of the data.

In some embodiments, as discussed above, the machine learning system uses a set of multiple machine learning models to code the patient data. In an embodiment, block 1110 may include selecting model(s) from among a set of models based on the context of the data, and/or processing it using multiple models. For example, in some embodiments, the machine learning system can use a model that was specifically trained or fine-tuned for the particular user or facility, as discussed above.

In at least one embodiment, the machine learning system can process different portions of the motion data using different models. For example, as discussed above, the machine learning system may process some aspects of the patient data using a first model, and other aspects using a second.

In some embodiments, as discussed above, the machine learning system may use hierarchical models, including an initial model to perform an initial classification of the patient data (e.g., to identify the broad category of the issue), followed by additional models at subsequent layers of the medical code.

At block 1115, the machine learning system determines whether the predicted medical code satisfies one or more defined criteria. In embodiments, this criteria may vary depending on the particular implementation. In some embodiments, the criteria includes evaluating of the confidence of the prediction. For example, if the model outputs a prediction confidence (or score of the predicted code), the machine learning system may determine whether this confidence (or score) meets or exceeds a defined threshold. In at least one embodiment, as discussed above, the model may be configured to output a probability or likelihood score for each possible medical code, and the predicted code may correspond to the highest-scored medical code. In some embodiments, at block 1115, the machine learning system can determine whether the highest score exceeds a threshold (e.g., greater than 50%).

In some embodiments, at block 1115, the machine learning system can determine whether the model output is consistent with the patient data. For example, some codes may be plainly contradictory of the patient data. In one such embodiment, the machine learning system may use a set of rules, or machine learning models, to identify such contradictions.

In at least one embodiment, at block 1115, the machine learning system can determine whether the model is in a test or initialization phase (as opposed to a fully deployed runtime phase). If the machine learning system is in a test phase, the machine learning system may determine to further evaluate the generated code, as discussed in more detail below. Similarly, in some embodiments, the machine learning system can randomly select some subset of the generated codes for further (manual) review.

If, at block 1115, the machine learning system determines that the criteria are satisfied, the method 1100 terminates at block 1135. If the machine learning system determines that one or more of the criteria are not satisfied, the method 1100 continues to block 1120, where the machine learning system prompts the user to confirm the appropriate medical code(s). Though this may require some manual effort from the user, it can nevertheless generally reduce the amount of time and effort required to ensure accurate and complete records are generated.

In some embodiments, the machine learning system may indicate the predicted code(s) and/or one or more of the next-highest scored alternatives, and ask the user to confirm which is correct (or to indicate the medical code, if the suggestion list does not include the proper code). As the user need only select from a shortened list of alternatives, they can generally do so more quickly and accurately than if they needed to input the code without such assistance.

At block 1125, the machine learning system receives the user response indicating the proper medical code(s) for the patient data. At block 1130, the machine learning system can then use this response to refine the model(s). For example, as discussed above, the user-provided actual medical code can be used as target output for the patient data, to be compared against the generated medical code. The model weights or other parameters can then be refined to more accurately generate subsequent codes. The method 1100 then terminates at block 1135.

Example Method for Diagnosing and Treating Patients using Machine Learning

Figure 12:
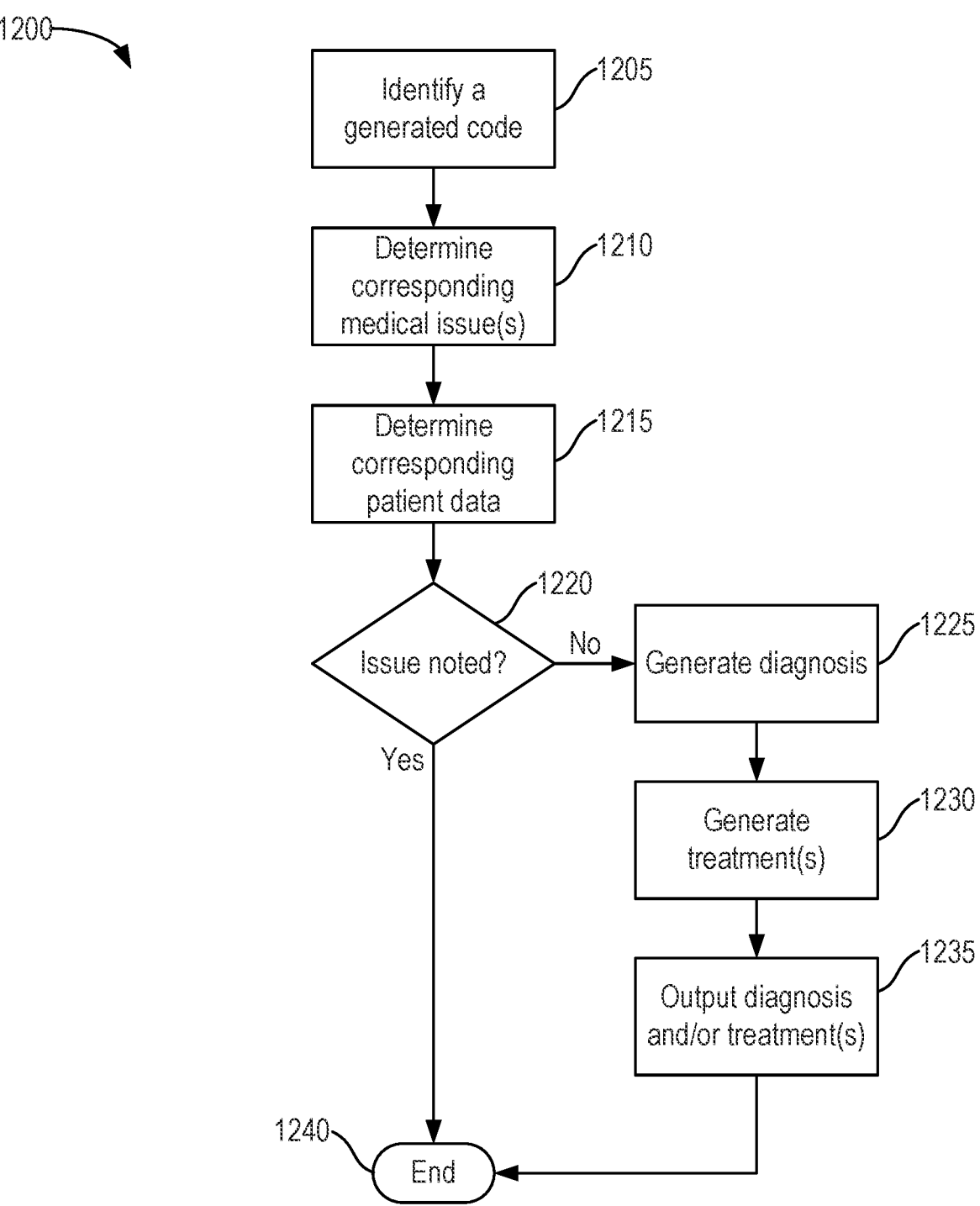
FIG. 12 is a flow diagram depicting an example method for diagnosing and treating patients using machine learning.

FIG. 12 is a flow diagram depicting an example method 1200 for diagnosing and treating patients using machine learning. In some embodiments, the method 1200 is performed by a machine learning system, such as machine learning system 120 of FIG. 1.

At block 1205, the machine learning system identifies a generated medical code. That is, the machine learning system can identify, in the patient data for a patient, a medical code that was generated using machine learning (e.g., by the machine learning system), as opposed to a medical code that was manually entered by a user.

At block 1210, the machine learning system determines the corresponding medical issue(s) associated with the generated medical code. For example, if the code relates to diabetes complications, the machine learning system can determine that the corresponding medical issues include diabetes in general, as well as the specific complications.

At block 1215, the machine learning system then identifies and evaluates patient data for the corresponding patient. That is, the machine learning system can identify the relevant patient (for whom the code was generated), and retrieve various patient data related to this patient (e.g., covering one or more prior interactions and/or more general patient information).

At block 1220, the machine learning system then evaluates the patient data to determine whether the determined medical issues (identified at block 1210) are reflected or noted in the patient data. For example, the machine learning system may evaluate assessments, diagnoses, and the like in order to determine whether it has been recognized (e.g., by a doctor) that the patient has diabetes. If the issue is noted or otherwise indicated in the data, the method 1200 terminates at block 1240.

If, at block 1220, the machine learning system determines that the determined medical issue(s) have not been indicated in the patient's data, the method 1200 continues to block 1225, where the machine learning system generates a diagnosis. In an embodiment, the machine learning system diagnoses the patient with the determined medical issue(s), such as diabetes. In some embodiments, the machine learning system may automatically enter this diagnosis into the patient's data. In others, it may output the diagnosis for confirmation or approval by the user.

At block 1230, the machine learning system generates one or more treatment(s) for the diagnosis. For example, as discussed above, the machine learning system may evaluate published literature, such as treatment guidelines, to identify which treatment(s) are appropriate for the specific disorder, and given the specific characteristics of the patient.

At block 1235, the machine learning system then outputs the diagnosis and/or treatment, such as to a user, for approval or confirmation. The method 1200 then terminates at block 1240.

In this way, the machine learning system can automatically perform personalized diagnosis of the patient, enabling identification and rapid treatment of illnesses and disorders that may have been otherwise undetected in the patient.

Figure 13:
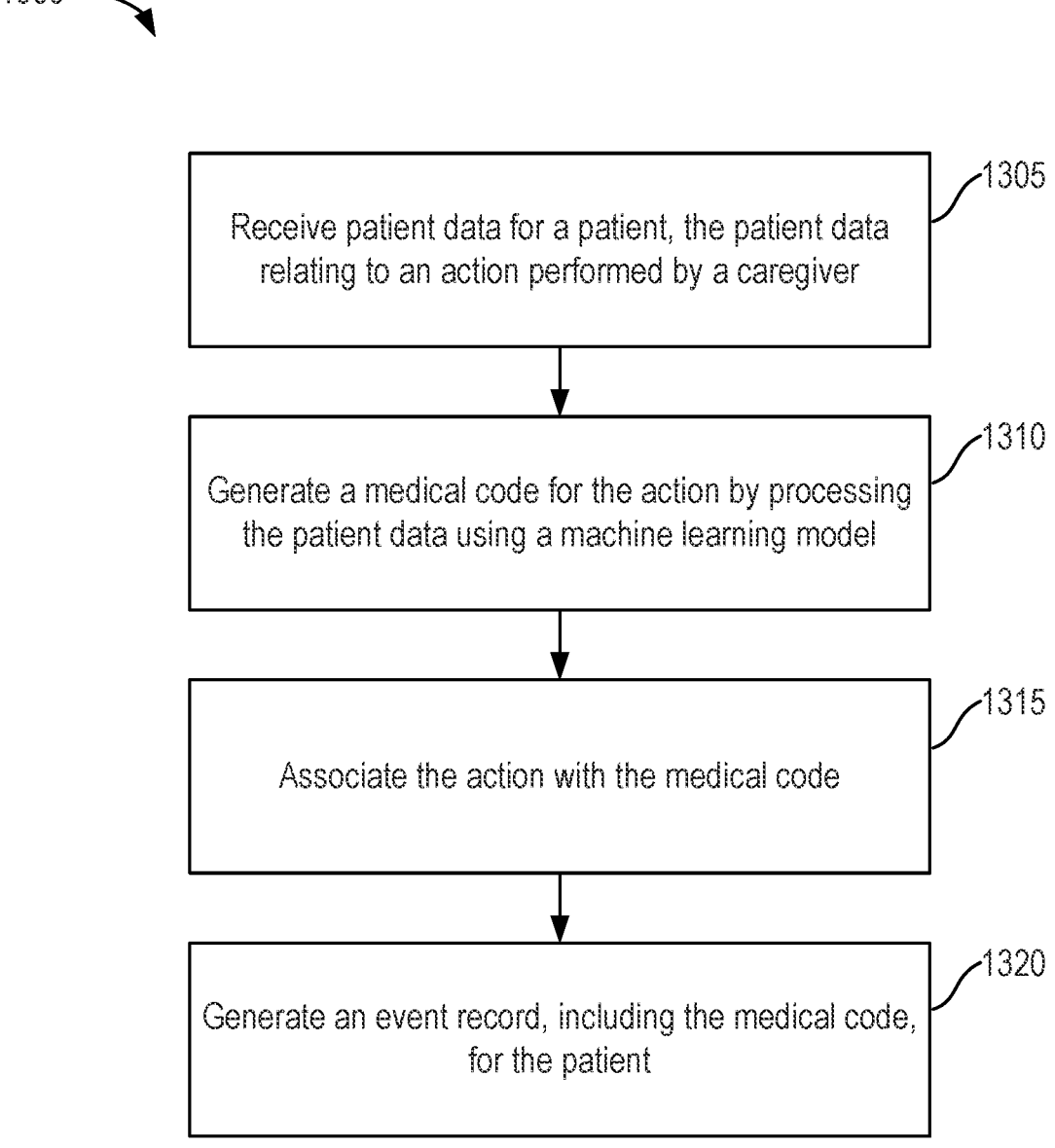
FIG. 13 is a flow diagram depicting an example method for generating medical codes and event records using machine learning.

Example Method for Generating Medical Codes and Event Records using Machine Learning FIG. 13 is a flow diagram depicting an example method 1300 for generating medical codes and event records using machine learning. In some embodiments, the method 1300 is performed by a machine learning system, such as machine learning system 120 of FIG. 1.

At block 1305, patient data for a patient is received, the patient data relating to an action performed by a caregiver.

At block 1310, a medical code is generated for the action by processing the patient data using a machine learning model.

At block 1315, the action is associated with the medical code.

At block 1320, an event record, including the medical code, is generated for the patient.

In some embodiments, the medical code indicates a medical issue for which the action was performed, and the patient data does not specify the medical issue.

In some embodiments, the medical code comprises an International Statistical Classification of Diseases and Related Health Problems (ICD) code.

In some embodiments, the method 1300 further includes outputting the medical code to a user for review.

In some embodiments, outputting the medical code is performed upon determining that the machine learning model is in a testing phase.

In some embodiments, the medical code indicates a medical issue of the patient, and outputting the medical code is performed upon determining that the patient data does not specify that the patient has the medical issue.

In some embodiments, the method 1300 further includes diagnosing the patient with the medical issue based on the medical code; and selecting a treatment for the patient based on the medical issue.

In some embodiments, the patient data comprises at least one of: a lab result, a caregiver assessment, one or more vital signs of the patient, a radiology result, a medication order, or one or more other actions performed for the patient.

Example Method for Training Machine Learning Models to Generate Medical Codes

Figure 14:
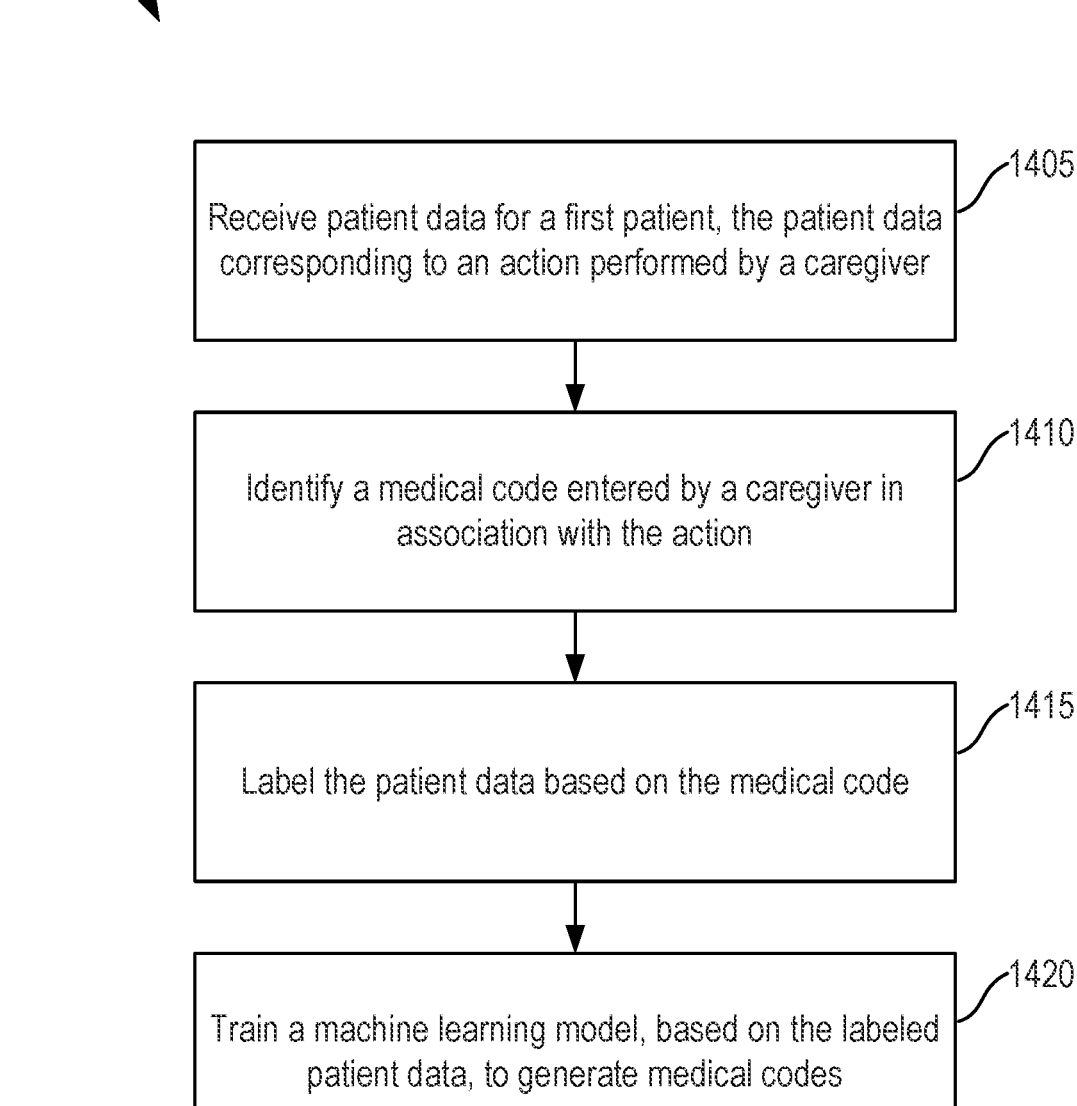
FIG. 14 is a flow diagram depicting an example method for training machine learning models to generate medical codes.

FIG. 14 is a flow diagram depicting an example method 1400 for training machine learning models to generate medical codes. In some embodiments, the method 1400 is performed by a machine learning system, such as machine learning system 120 of FIG. 1.

At block 1405, patient data for a first patient is received, the patient data corresponding to an action performed by a caregiver.

At block 1410, a medical code entered by a caregiver in association with the action is identified.

At block 1415, the patient data is labeled based on the medical code.

At block 1420, a machine learning model is trained, based on the labeled patient data, to generate medical codes.

In some embodiments, the method 1400 further includes generating a new medical code by processing patient data for a second patient using the machine learning model, wherein the new medical code indicates a medical issue, and diagnosing the second patient with the medical issue based on determining that the patient data for the second patient does not specify that the second patient has the medical issue.

In some embodiments, the method 1400 further includes generating a new medical code by processing patient data for a second patient using the machine learning model, wherein the new medical code indicates a medical issue, and selecting a treatment for the second patient based on the medical issue.

In some embodiments, the method 1400 further includes generating a new medical code by processing patient data for a second patient using the machine learning model, wherein the new medical code indicates a medical issue, diagnosing the second patient with the medical issue based on determining that the patient data for the second patient does not specify that the second patient has the medical issue, and selecting a treatment for the second patient based on the medical issue.

In some embodiments, the medical code indicates a medical issue for which the action was performed, and the patient data does not specify the medical issue.

In some embodiments, the medical code comprises an International Statistical Classification of Diseases and Related Health Problems (ICD) code.

In some embodiments, the method 1400 further includes generating a predicted medical code by processing patient data for a second patient using the machine learning model, outputting the predicted medical code to a user, receiving, from the user, an indication that the predicted medical code is accurate, and refining the machine learning model based on the indication.

In some embodiments, the method 1400 further includes generating a predicted medical code by processing patient data for a second patient using the machine learning model, outputting the predicted medical code to a user, receiving, from the user, an indication that the predicted medical code is not accurate, and refining the machine learning model based on the indication.

In some embodiments, the indication includes a correct medical code for the patient data for the second patient, and refining the machine learning model comprises training the machine learning model to predict the correct medical code for the patient data for the second patient.

In some embodiments, the patient data comprises at least one of: a lab result, a caregiver assessment, one or more vital signs of the patient, a radiology result, a medication order, or one or more other actions performed for the patient.

Example Processing System for Improved Machine Learning Models

Figure 15:
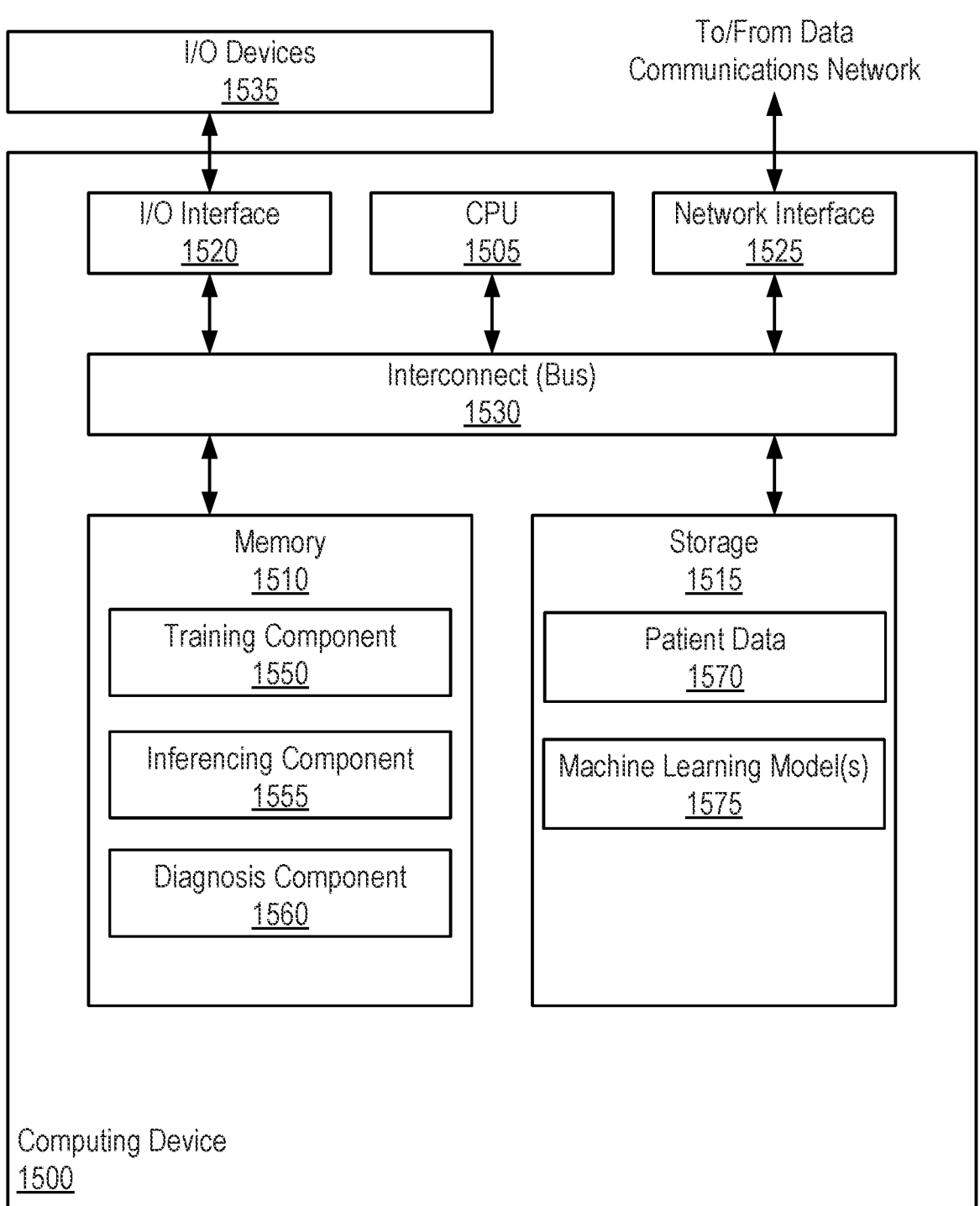
FIG. 15 depicts an example computing device configured to perform various aspects of the present disclosure.

FIG. 15 depicts an example computing device 1500 configured to perform various aspects of the present disclosure. Although depicted as a physical device, in embodiments, the computing device 1500 may be implemented using virtual device(s), and/or across a number of devices (e.g., in a cloud environment). In one embodiment, the computing device 1500 corresponds to the machine learning system 120 of FIG. 1.

As illustrated, the computing device 1500 includes a CPU 1505, memory 1510, storage 1515, a network interface 1525, and one or more I/O interfaces 1520. In the illustrated embodiment, the CPU 1505 retrieves and executes programming instructions stored in memory 1510, as well as stores and retrieves application data residing in storage 1515. The CPU 1505 is generally representative of a single CPU and/or GPU, multiple CPUs and/or GPUs, a single CPU and/or GPU having multiple processing cores, and the like. The memory 1510 is generally included to be representative of a random access memory. Storage 1515 may be any combination of disk drives, flash-based storage devices, and the like, and may include fixed and/or removable storage devices, such as fixed disk drives, removable memory cards, caches, optical storage, network attached storage (NAS), or storage area networks (SAN).

In some embodiments, I/O devices 1535 (such as keyboards, monitors, etc.) are connected via the I/O interface(s) 1520. Further, via the network interface 1525, the computing device 1500 can be communicatively coupled with one or more other devices and components (e.g., via a network, which may include the Internet, local network(s), and the like). As illustrated, the CPU 1505, memory 1510, storage 1515, network interface(s) 1525, and I/O interface(s) 1520 are communicatively coupled by one or more buses 1530.

In the illustrated embodiment, the memory 1510 includes a training component 1550, an inferencing component 1555, and a diagnosis component 1560, which may perform one or more embodiments discussed above. Although depicted as discrete components for conceptual clarity, in embodiments, the operations of the depicted components (and others not illustrated) may be combined or distributed across any number of components. Further, although depicted as software residing in memory 1510, in embodiments, the operations of the depicted components (and others not illustrated) may be implemented using hardware, software, or a combination of hardware and software.

In one embodiment, the training component 1550 is used to generate labeled data and/or train the machine learning model(s), such as by using the workflow 100 of FIG. 1, the workflow 200 of FIG. 2, the workflow 300 of FIG. 3, the workflow 400 of FIG. 4, the method 700 of FIG. 7, the method 800 of FIG. 8, the method 900 of FIG. 9, and/or the method 1400 of FIG. 14. The inferencing component 1555 may be configured to use the models to classify motion data using trained models, such as by using the workflow 500 of FIG. 5, the workflow 600 of FIG. 6, method 1000 of FIG. 10, the method 1100 of FIG. 11, the method 1100 of FIG. 11, the method 1200 of FIG. 12, and/or the method 1300 of FIG. 13. The diagnosis component 1560 (or one or more other components that are not depicted) may use the generated codes to generate event record, diagnose the patient, and/or generate treatments, such as by using the workflow 600 of FIG. 6, and/or the method 1200 of FIG. 12.

In the illustrated example, the storage 1515 includes patient data 1570 (which may correspond to labeled patient data used to train and/or evaluate the models, as well as generated event records), as well as one or more machine learning model(s) 1575. Although depicted as residing in storage 1515, the historical data 1570 and machine learning model(s) 1575 may be stored in any suitable location, including memory 1510.

EXAMPLE CLAUSES

Implementation examples are described in the following numbered clauses:

Clause 1: A method, comprising: receiving patient data for a patient, the patient data relating to an action performed by a caregiver; receiving motion data collected, using one or more wearable sensors of the caregiver, while the caregiver performed the action; generating a medical code for the action by processing the patient data and the motion data using one or more machine learning models, wherein the medical code indicates a medical issue of the patient; associating the action with the medical code; generating an event record, including the medical code, for the patient; and upon determining that the patient data does not specify that the patient has the medical issue, outputting the medical code to a user for review.

Clause 2: The method of Clause 1, further comprising: diagnosing the patient with the medical issue based on the medical code; and selecting a treatment for the patient based on the medical issue.

Clause 3: The method of any one of Clauses 1-2, wherein the medical code comprises an International Statistical Classification of Diseases and Related Health Problems (ICD) code.

Clause 4: The method of any one of Clauses 1-3, wherein outputting the medical code is performed upon further determining that at least one of the one or more machine learning models is in a testing phase.

Clause 5: The method of any one of Clauses 1-4, wherein the patient data comprises at least one of: (i) a lab result; (ii) a caregiver assessment; (iii) one or more vital signs of the patient; (iv) a radiology result; (v) a medication order; or (vi) one or more other actions performed for the patient.

Clause 6: A method, comprising: receiving patient data for a first patient, the patient data corresponding to an action performed by a caregiver; identifying a medical code entered by a caregiver in association with the action; labeling the patient data based on the medical code; and training a machine learning model, based on the labeled patient data, to generate medical codes.

Clause 7: The method of Clause 6, further comprising: generating a new medical code by processing patient data for a second patient using the machine learning model, wherein the new medical code indicates a medical issue; and diagnosing the second patient with the medical issue based on determining that the patient data for the second patient does not specify that the second patient has the medical issue.

Clause 8: The method of any one of Clauses 6-7, further comprising: generating a new medical code by processing patient data for a second patient using the machine learning model, wherein the new medical code indicates a medical issue; and selecting a treatment for the second patient based on the medical issue.

Clause 9: The method of any one of Clauses 6-8, further comprising: generating a new medical code by processing patient data for a second patient using the machine learning model, wherein the new medical code indicates a medical issue; diagnosing the second patient with the medical issue based on determining that the patient data for the second patient does not specify that the second patient has the medical issue; and selecting a treatment for the second patient based on the medical issue.

Clause 10: The method of any one of Clauses 6-9, wherein: the medical code indicates a medical issue for which the action was performed, and the patient data does not specify the medical issue.

Clause 11: The method of any one of Clauses 6-10, wherein the medical code comprises an International Statistical Classification of Diseases and Related Health Problems (ICD) code.

Clause 12: The method of any one of Clauses 6-11, further comprising: generating a predicted medical code by processing patient data for a second patient using the machine learning model; outputting the predicted medical code to a user; receiving, from the user, an indication that the predicted medical code is accurate; and refining the machine learning model based on the indication.

Clause 13: The method of any one of Clauses 6-12, further comprising: generating a predicted medical code by processing patient data for a second patient using the machine learning model; outputting the predicted medical code to a user; receiving, from the user, an indication that the predicted medical code is not accurate; and refining the machine learning model based on the indication.

Clause 14: The method of any one of Clauses 6-13, wherein: the indication includes a correct medical code for the patient data for the second patient, and refining the machine learning model comprises training the machine learning model to predict the correct medical code for the patient data for the second patient.

Clause 15: The method of any one of Clauses 6-14, wherein the patient data comprises at least one of: (i) a lab result; (ii) a caregiver assessment; (iii) one or more vital signs of the first patient; (iv) a radiology result; (v) a medication order; or (vi) one or more other actions performed for the first patient.

Clause 16: A method, comprising: receiving patient data for a patient, the patient data relating to an action performed by a caregiver; generating a medical code for the action by processing the patient data using a machine learning model; associating the action with the medical code; and generating an event record, including the medical code, for the patient.

Clause 17: The method of Clause 16, wherein: the medical code indicates a medical issue for which the action was performed, and the patient data does not specify the medical issue.

Clause 18: The method of any one of Clauses 16-17, wherein the medical code comprises an International Statistical Classification of Diseases and Related Health Problems (ICD) code.

Clause 19: The method of any one of Clauses 16-18, further comprising outputting the medical code to a user for review.

Clause 20: The method of any one of Clauses 16-19, wherein outputting the medical code is performed upon determining that the machine learning model is in a testing phase.

Clause 21: The method of any one of Clauses 16-20, wherein: the medical code indicates a medical issue of the patient, and outputting the medical code is performed upon determining that the patient data does not specify that the patient has the medical issue.

Clause 22: The method of any one of Clauses 16-21, further comprising: diagnosing the patient with the medical issue based on the medical code; and selecting a treatment for the patient based on the medical issue.

Clause 23: The method of any one of Clauses 16-22, wherein the patient data comprises at least one of: (i) a lab result; (ii) a caregiver assessment; (iii) one or more vital signs of the patient; (iv) a radiology result; (v) a medication order; or (vi) one or more other actions performed for the patient.

Clause 24: A system, comprising: a memory comprising computer-executable instructions; and one or more processors configured to execute the computer-executable instructions and cause the processing system to perform a method in accordance with any one of Clauses 1-23.

Clause 25: A system, comprising means for performing a method in accordance with any one of Clauses 1-23.

Clause 26: A non-transitory computer-readable medium comprising computer-executable instructions that, when executed by one or more processors of a processing system, cause the processing system to perform a method in accordance with any one of Clauses 1-23.

Clause 27: A computer program product embodied on a computer-readable storage medium comprising code for performing a method in accordance with any one of Clauses 1-23.

ADDITIONAL CONSIDERATIONS

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications or systems (e.g., the machine learning system 120) or related data available in the cloud. For example, the machine learning system 120 could execute on a computing system in the cloud and train and/or use machine learning models. In such a case, the machine learning system 120 could train models to generate medical codes, and store the models at a storage location in the cloud. Doing so allows a user to access this information from any computing system attached to a network connected to the cloud (e.g., the Internet).

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A method, comprising:
receiving patient data for a patient, the patient data relating to an action performed by a caregiver;
collecting, by one or more wearable devices of the caregiver, motion data, wherein the motion data is collected using one or more accelerometers of the one or more wearable devices while the caregiver performed the action, and wherein the motion data indicates orientation and movement of one or more hands of the caregiver while performing the action;
in response to determining that a current time is within a first window of time during which patient data and motion data from during a corresponding second window of time are to be evaluated to balance computational load:
transmitting the motion data to a machine learning system;
evaluating the motion data using an action machine learning model to identify the action performed by the caregiver; and
generating a medical code for the action by processing the patient data and the identified action using a plurality of code machine learning models, wherein the medical code indicates a medical issue of the patient, comprising:
generating a first code classification at a first level of a code hierarchy based on processing the patient data and the identified action using a first code machine learning model trained for the first level; and
generating the medical code based on processing the patient data and the identified action using a second code machine learning model trained for a second level of the code hierarchy;

associating the action with the medical code;
generating an event record, including the medical code, for the patient; and
upon determining that the patient data does not specify that the patient has the medical issue, outputting the medical code to a user for review.

2. The method of claim 1, further comprising:
diagnosing the patient with the medical issue based on the medical code; and
selecting a treatment for the patient based on the medical issue.

3. The method of claim 1, wherein the medical code comprises an International Statistical Classification of Diseases and Related Health Problems (ICD) code.

4. The method of claim 1, wherein outputting the medical code is performed upon further determining that at least one of the plurality of code machine learning models is in a testing phase.

5. The method of claim 1, wherein the patient data comprises at least one of:
(i) a lab result;
(ii) a caregiver assessment;
(iii) one or more vital signs of the patient;
(iv) a radiology result;
(v) a medication order; or
(vi) one or more other actions performed for the patient.

6. A method, comprising:
receiving patient data for a first patient, the patient data corresponding to an action performed by a caregiver;
collecting, by one or more wearable devices of the caregiver, motion data, wherein the motion data is collected using one or more accelerometers of the one or more wearable devices while the caregiver performed the action, and wherein the motion data indicates orientation and movement of one or more hands of the caregiver while performing the action;
in response to determining that a current time is within a first window of time during which patient data and motion data from during a corresponding second window of time are to be evaluated to balance computational load:
transmitting the motion data to a machine learning system;
evaluating the motion data using an action machine learning model to identify the action performed by the caregiver;
identifying a medical code entered by the caregiver in association with the action;
labeling the patient data and the identified action based on the medical code; and
training a plurality of code machine learning models, based on the labeled patient data and the identified action, to generate medical codes, comprising:
training a first code machine learning model to generate first code classifications at a first level of a code hierarchy; and
training a second code machine learning model to generate medical codes at a second level of the code hierarchy.

7. The method of claim 6, further comprising:
generating a new medical code by processing patient data for a second patient using one or more of the plurality of code machine learning models, wherein the new medical code indicates a medical issue; and diagnosing the second patient with the medical issue based on determining that the patient data for the second patient does not specify that the second patient has the medical issue.

8. The method of claim 6, further comprising:

generating a new medical code by processing patient data for a second patient using one or more of the plurality of code machine learning models, wherein the new medical code indicates a medical issue; and selecting a treatment for the second patient based on the medical issue.

9. The method of claim 6, further comprising:

generating a new medical code by processing patient data for a second patient using one or more of the plurality of code machine learning models, wherein the new medical code indicates a medical issue;

diagnosing the second patient with the medical issue based on determining that the patient data for the second patient does not specify that the second patient has the medical issue; and selecting a treatment for the second patient based on the medical issue.

10. The method of claim 6, wherein:

the medical code indicates a medical issue for which the action was performed, and the patient data does not specify the medical issue.

11. The method of claim 6, wherein the medical code comprises an International Statistical Classification of Diseases and Related Health Problems (ICD) code.

12. The method of claim 6, further comprising:

generating a predicted medical code by processing patient data for a second patient using one or more of the plurality of code machine learning models;

outputting the predicted medical code to a user;

receiving, from the user, an indication that the predicted medical code is accurate; and refining one or more of the plurality of code machine learning models based on the indication.

13. The method of claim 6, further comprising:

generating a predicted medical code by processing patient data for a second patient using one or more of the plurality of code machine learning models;

outputting the predicted medical code to a user;

receiving, from the user, an indication that the predicted medical code is not accurate; and refining one or more of the plurality of code machine learning models based on the indication.

14. The method of claim 13, wherein:

the indication includes a correct medical code for the patient data for the second patient, and refining the one or more of the plurality of code machine learning models comprises training the one or more of the plurality of code machine learning models to predict the correct medical code for the patient data for the second patient.

15. The method of claim 6, wherein the patient data comprises at least one of:

(i) a lab result;

(ii) a caregiver assessment;

(iii) one or more vital signs of the first patient;

(iv) a radiology result;

(v) a medication order; or (vi) one or more other actions performed for the first patient.

16. A method, comprising:

receiving patient data for a patient, the patient data relating to an action performed by a caregiver;

collecting, by one or more wearable devices of the caregiver, motion data, wherein the motion data is collected using one or more accelerometers of the one or more wearable devices, while the caregiver performed the action, and wherein the motion data indicates orientation and movement of one or more hands of the caregiver while performing the action;

in response to determining that a current time is within a first window of time during which patient data and motion data from during a corresponding second window of time are to be evaluated to balance computational load:

transmitting the motion data to a machine learning system;

evaluating the motion data using an action machine learning model to identify the action performed by the caregiver; and generating a medical code for the action by processing the patient data and the identified action using a plurality of code machine learning models, wherein the medical code indicates a medical issue of the patient, comprising:

generating a first code classification at a first level of a code hierarchy based on processing the patient data and the identified action using a first code machine learning model trained for the first level; and generating the medical code based on processing the patient data and the identified action using a second code machine learning model trained for a second level of the code hierarchy;

associating the action with the medical code; and generating an event record, including the medical code, for the patient.

17. The method of claim 16, wherein:

the medical code indicates a medical issue for which the action was performed, and the patient data does not specify the medical issue.

18. The method of claim 16, wherein the medical code comprises an International Statistical Classification of Diseases and Related Health Problems (ICD) code.

19. The method of claim 16, further comprising outputting the medical code to a user for review.

20. The method of claim 19, wherein outputting the medical code is performed upon determining that one or more of the plurality of code machine learning models is in a testing phase.

21. The method of claim 19, wherein:

the medical code indicates a medical issue of the patient, and outputting the medical code is performed upon determining that the patient data does not specify that the patient has the medical issue.

22. The method of claim 21, further comprising:

diagnosing the patient with the medical issue based on the medical code; and selecting a treatment for the patient based on the medical issue.

23. The method of claim 16, wherein the patient data comprises at least one of:

(i) a lab result;

(ii) a caregiver assessment;

(iii) one or more vital signs of the patient;

(iv) a radiology result;

(v) a medication order; or (vi) one or more other actions performed for the patient.

24. A method, comprising:

receiving patient data for a patient, the patient data relating to an action performed by a caregiver;

collecting, by one or more wearable devices of the caregiver, motion data, wherein the motion data is collected using one or more accelerometers of the one or more wearable devices, while the caregiver performed the action, and wherein the motion data indicates orientation and movement of one or more hands of the caregiver while performing the action;

in response to determining that a current time is within a first window of time during which patient data and motion data from during a corresponding second window of time are to be evaluated to balance computational load:

transmitting the motion data to a machine learning system;

evaluating the motion data using an action machine learning model to identify the action performed by the caregiver; and generating a medical code for the action by processing the patient data and the identified action using one or more code machine learning models, wherein the medical code indicates a medical issue of the patient, comprising:

identifying an expected payer for the action performed by the caregiver;

accessing a corresponding payer-specific code machine learning model trained for the expected payer; and generating the medical code based on processing the patient data and the identified action using the payer-specific code machine learning model;

associating the action with the medical code;

generating an event record, including the medical code, for the patient; and upon determining that the patient data does not specify that the patient has the medical issue, outputting the medical code to a user for review.

* * * * *